(12) United States Patent
Timnak et al.

(10) Patent No.: US 11,547,776 B2
(45) Date of Patent: Jan. 10, 2023

(54) GRADED POROUS SCAFFOLDS AS IMMUNOMODULATORY WOUND PATCHES

(71) Applicant: Temple University—Of The Commonwealth System of Higher Education, Philadelphia, PA (US)

(72) Inventors: Azadeh Timnak, Philadelphia, PA (US); Peter I. Lelkes, Cherry Hill, NJ (US); Yah-el H. Har-el, Philadelphia, PA (US)

(73) Assignee: Temple University-Of The Commonwealth System of Higher Education, Philadelphia, PA (US)

( * ) Notice: Subject to any disclaimer, the term of this patent is extended or adjusted under 35 U.S.C. 154(b) by 247 days.

(21) Appl. No.: 16/608,381

(22) PCT Filed: Apr. 26, 2018

(86) PCT No.: PCT/US2018/029519
§ 371 (c)(1),
(2) Date: Oct. 25, 2019

(87) PCT Pub. No.: WO2018/200776
PCT Pub. Date: Nov. 1, 2018

(65) Prior Publication Data
US 2021/0046213 A1 Feb. 18, 2021

Related U.S. Application Data

(60) Provisional application No. 62/490,148, filed on Apr. 26, 2017.

(51) Int. Cl.
*A61L 27/22* (2006.01)
*A61L 27/26* (2006.01)
*A61L 27/56* (2006.01)
*D01D 5/00* (2006.01)

(52) U.S. Cl.
CPC ............. *A61L 27/227* (2013.01); *A61L 27/26* (2013.01); *A61L 27/56* (2013.01); *D01D 5/003* (2013.01); *D10B 2509/022* (2013.01)

(58) Field of Classification Search
CPC ..................................................... A61L 27/227
See application file for complete search history.

(56) References Cited

U.S. PATENT DOCUMENTS

2009/0074832 A1* 3/2009 Zussman ............. A61L 27/3821
606/151
2013/0302296 A1* 11/2013 Lue ....................... A61K 38/482
424/93.44

* cited by examiner

*Primary Examiner* — Carlos A Azpuru
(74) *Attorney, Agent, or Firm* — Riverside Law LLP

(57) ABSTRACT

The present invention provides porous biomimetic scaffolds and methods for making the same. The scaffolds have graded pore sizes for enhanced cell penetration. The scaffolds are useful for wound regeneration by facilitating cell penetration into the scaffold interior and due to their inherent immunomodulatory effects. The scaffolds have tissue modeling specification by mimicking the inherent stratified structure of certain tissues.

12 Claims, 21 Drawing Sheets

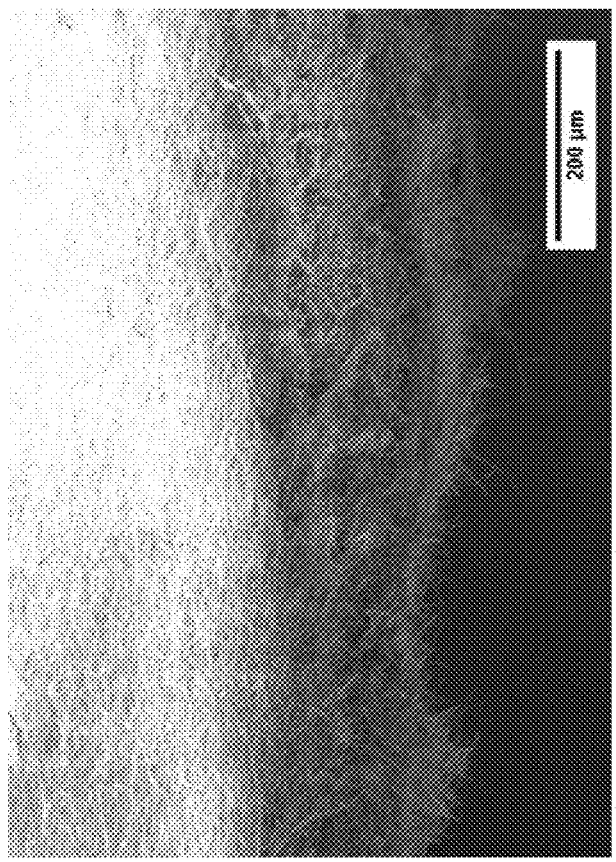
Figure 5B
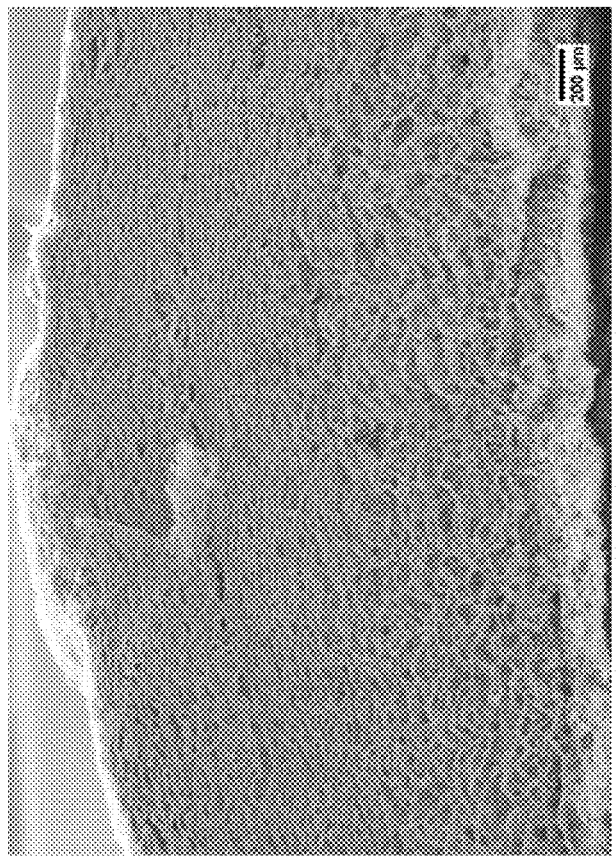
Figure 5A
Figure 5A – Figure 5B

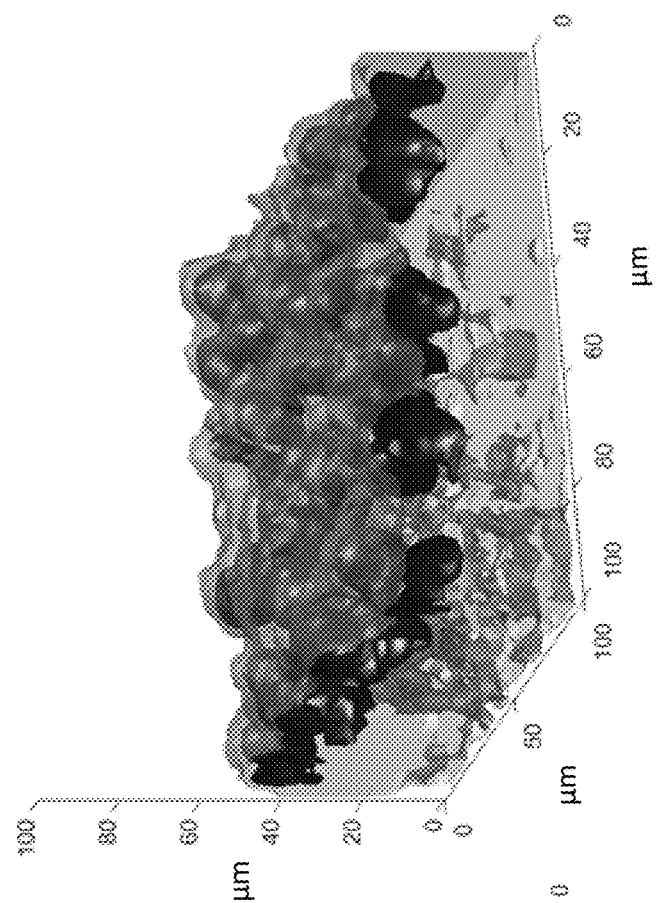
Figure 7B
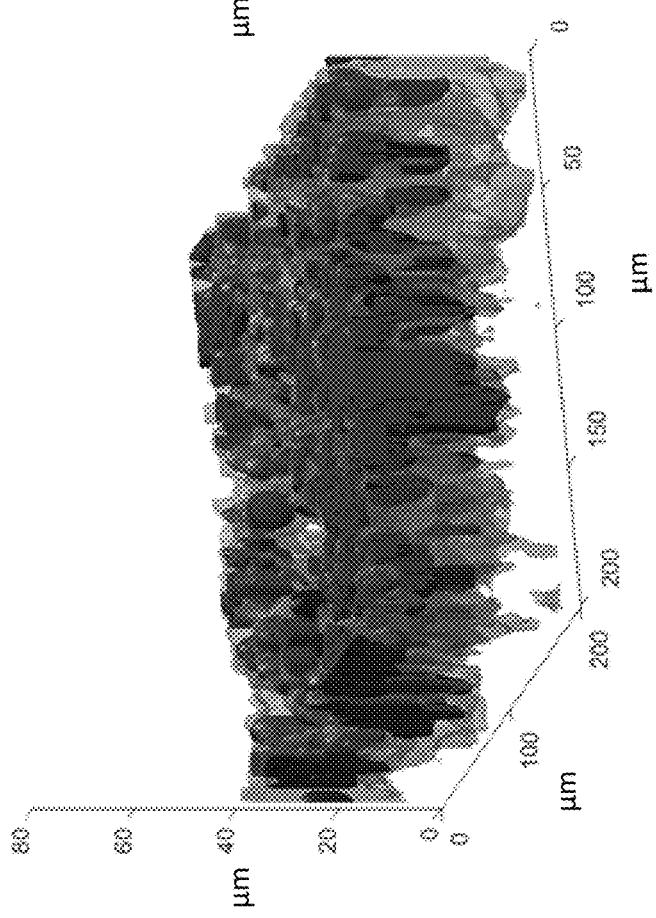
Figure 7A
Figure 7A – Figure 7B

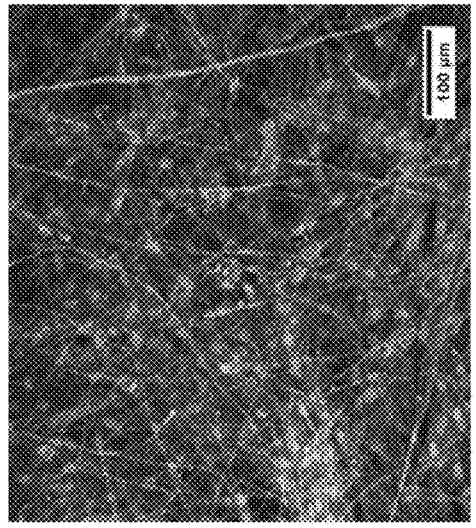
Figure 10B
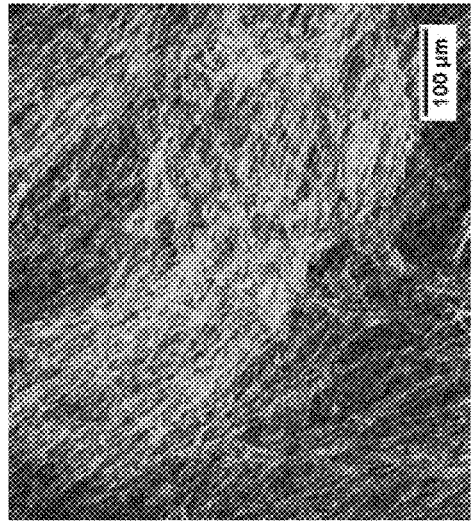
Figure 10A
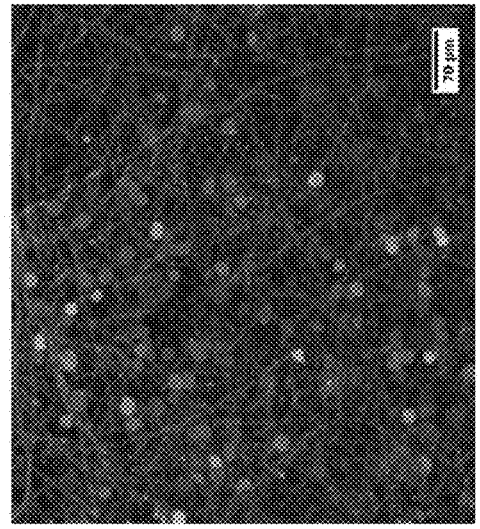
Figure 10D
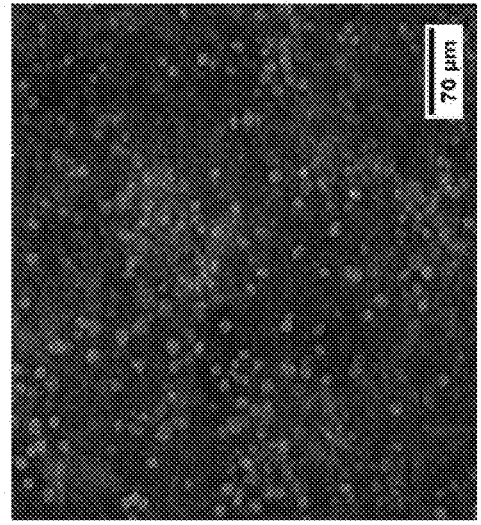
Figure 10C
Figure 10A – Figure 10D

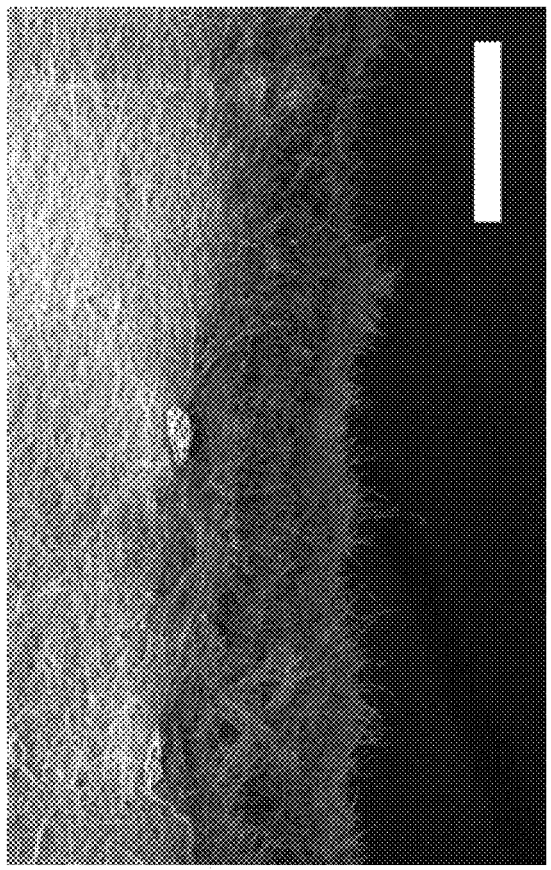
Figure 12B
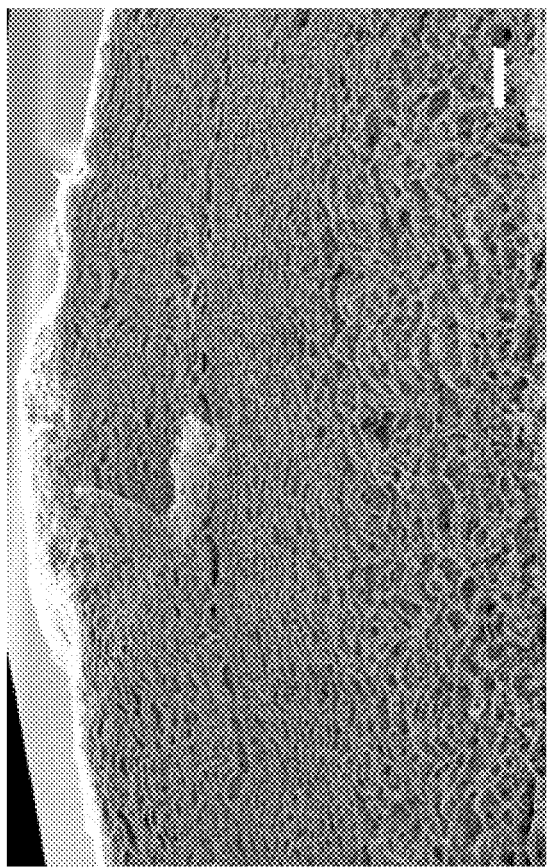
Figure 12A
Figure 12A – Figure 12B

Scale bar is 50 μm

| Type of scaffold | Pore diameter (μm) |
|---|---|
| GPF, small pore side | 7.8 ± 2.5 |
| GPF, mid layer | 21.4 ± 10.3 |
| GPF, large pore side | 58.02 ± 23.6 |
| Control SPI | 4.2 ± 1.3 |

* denotes *p*-value < 0.05

GRADED POROUS SCAFFOLDS AS IMMUNOMODULATORY WOUND PATCHES

CROSS-REFERENCE TO RELATED APPLICATIONS

This application is the U.S. national phase application filed under 35 U.S.C. § 371 claiming benefit to International Patent Application No. PCT/US18/29519 filed Apr. 26, 2018, which is entitled to priority under 35 U.S.C. § 119(e) to U.S. Provisional Patent Application No. 62/490,148, filed Apr. 26, 2017, the contents of which are each incorporated by reference herein in their entirety.

BACKGROUND OF THE INVENTION

Chronic wound care imposes enormous financial burden to both the US healthcare system and personal payers. Currently, the annual cost associated with non-healing/hard to heal skin wounds amounts to about 25 billion dollars (Witherel C E et al., Wound Repair and Regeneration 24.3 (2016): 514-524). However, in spite of all the costs, the patients' need for living a normal life without any pain or scarring are barely met. While autografting is one of the more common method practiced in skin replacement, morbidity, mortality, and size limitations in terms of the area of donor skin available for transplantation are still issues.

Alternative treatment modalities include the application of bioactive wound dressings, negative pressure wound therapy (NPWT), or bioengineered skin replacements. Application of wound dressings while effectively balancing the moisture of the wound bed can still lead to scarring and necrosis of the tissues. NPWT offers benefits such as faster granulation tissue formation and reduction in wound size, which ultimately leads to a decrease in the necessity to amputate the wounded tissue (Huang C et al., Current problems in surgery 51.7 (2014): 301-331; Bruhin A et al., International Journal of Surgery 12.10 (2014): 1105-1114; Li T et al., Experimental and therapeutic medicine 11.3 (2016): 769-776). However, NPWT is associated with several clinical caveats (Huang C et al., Current problems in surgery 51.7 (2014): 301-331; Bruhin A et al., International Journal of Surgery 12.10 (2014): 1105-1114; Orgill D P et al., International wound journal 10.s1 (2013): 15-19). According to recent FDA alerts, NPWT can occasionally lead to severe complications including bleeding and infections.

Application of bioengineered scaffolds in animal models seems to play a role in the restoration of skin appendages, which is not reported in the skin wounds treated with the other two techniques (Har-el Y et al., Wound Medicine 5 (2014): 9-15; Sundaramurthi D et al., Polymer Reviews 54.2 (2014): 348-376). Reestablishment of the skin appendages represents initiation of tissue regeneration, the final and desired stage of the healing process. Prolonged inflammation is a major obstacle to remodeling and regeneration of healing tissues (Wang Z et al., Biomaterials 35.22 (2014): 5700-5710; Mantovani A et al., The Journal of pathology 229.2 (2013): 176-185; Badylak S F et al., Tissue Engineering Part A 14.11 (2008): 1835-1842).

There is a need in the art for scaffolds with improved porous structures. The present invention meets this need.

SUMMARY OF THE INVENTION

In one aspect, the invention relates to a scaffold comprising: a porous material comprising: soy protein isolate (SPI) fibers having a first surface, a second surface, and a thickness therebetween; wherein the average pore size at the first surface is smaller than the average pore size at the second surface; and wherein the average pore size gradually increases through the material from the first surface to the second surface.

In one embodiment, the plant protein is selected from the group consisting of soy protein isolate, wheat gluten, corn zein, and pea protein. In one embodiment, the fibers have a diameter between 0.5 µm and 5 µm. In one embodiment, the scaffold has a thickness between 500 µm and 2000 µm. In one embodiment, the average pore size of the first surface is between 1 µm and 20 µm in diameter. In one embodiment, the average pore size of the second surface is between 10 µm and 200 µm. In one embodiment, the gradual increase of the average pore size is linear. In one embodiment, the gradual increase of the average pore size is nonlinear.

In one embodiment, the scaffold is capable of supporting cell growth. In one embodiment, the scaffold further comprises at least one cell. In one embodiment, the scaffold further comprises at least one material selected from the group consisting of: fibronectin, laminin, collagen, glycoprotein, thrombospondin, elastin, fibrillin, mucopolysaccharide, glycolipid, heparin sulfate, chondroitin sulfate, keratin sulfate, glycosaminoglycan, hyaluronic acid, proteoglycan, vitronectin, poly-D-lysine, and polysaccharide. In one embodiment, the scaffold further comprises at least one material selected from the group consisting of poly(epsilon-caprolactone) (PCL), poly(lactic acid) (PLA), poly(glycolic acid) (PGA), copolymers poly (lactide-co-glycolide) (PLGA), polyaniline, and poly(ethylene oxide) (PEO).

In another aspect, the invention relates to a method of making a graded porous scaffold, comprising the steps of: electroprocessing a plant protein solution with a sacrificial material solution, the plant protein solution and the sacrificial material being deposited simultaneously and separately to a rotating substrate, to form a composite scaffold; removing the sacrificial material from the composite scaffold to form a plant protein scaffold; hydrating the plant protein scaffold in an aqueous solution; freezing the plant protein scaffold; and lyophilizing the frozen plant protein scaffold to form a graded porous scaffold.

In one embodiment, the electroprocessing is electrospinning. In one embodiment, the SPI solution comprises SPI dissolved in 1,1,1,3,3,3,-Hexafluoro-2-propanol. In one embodiment, the sacrificial material comprises a water-soluble material. In one embodiment, the water-soluble material is PEO dissolved in ethanol. In one embodiment, the aqueous solution is water. In one embodiment, the freezing step is performed at −80° C. for 2 hours. In one embodiment, the lyophilizing step is performed at −60° C. and 0.08 mbar.

BRIEF DESCRIPTION OF THE DRAWINGS

The following detailed description of embodiments of the invention will be better understood when read in conjunction with the appended drawings. It should be understood, however, that the invention is not limited to the precise arrangements and instrumentalities of the embodiments shown in the drawings.

FIG. 5A and FIG. 5B depict cross-sectional views of: a graded hydrated-lyophilized (GHL) scaffold (FIG. 5A) versus a regularly spun SPI scaffold (FIG. 5B) taken using a scanning electron microscope at the accelerating voltage of 30 kV.

FIG. 7A and FIG. 7B depict 3D-reconstructed laser scanning confocal images using MATLAB showing RAW264.7 cell penetration into an HL scaffold (FIG. 7A) and a regularly spun SPI scaffold (FIG. 7B) 24 hours post seeding. Cell nuclei are in blue, scaffolds are in green. Axes units are in μm.

FIG. 10A through FIG. 10D depict the results of cell viability 5 days post-seeding for human dermal fibroblast on GHL scaffold (FIG. 10A) and regularly spun SPI (FIG. 10B), and for THP-1 cells on GHL scaffold (FIG. 10C) and regularly spun SPI (FIG. 10D).

FIG. 12A through FIG. 12C compare pore sizes between a GHL scaffold and a regularly spun SPI scaffold. FIG. 12A is a cross-sectional view of a GHL scaffold. FIG. 12B is a cross-sectional view of a regularly spun SPI scaffold. Cross-sectional views were taken using a scanning electron microscope. FIG. 12C is a graph showing the range of pore sizes in different regions of a GHL scaffold and a regularly spun SPI scaffold. Brackets shows the two groups that were statistically compared. In this case, Mid is compared to Electrospun SPI and Bottom is compared to Electrospun SPI. Double asterisk denotes the p value of equal or less than 0.01. In statistical analysis a p-value determines the significance of the results. A p-value of less than 0.01 indicates that two groups of comparison are significantly different with a certainty of 99%.

DETAILED DESCRIPTION

Figures 1A, 1B, 1C:
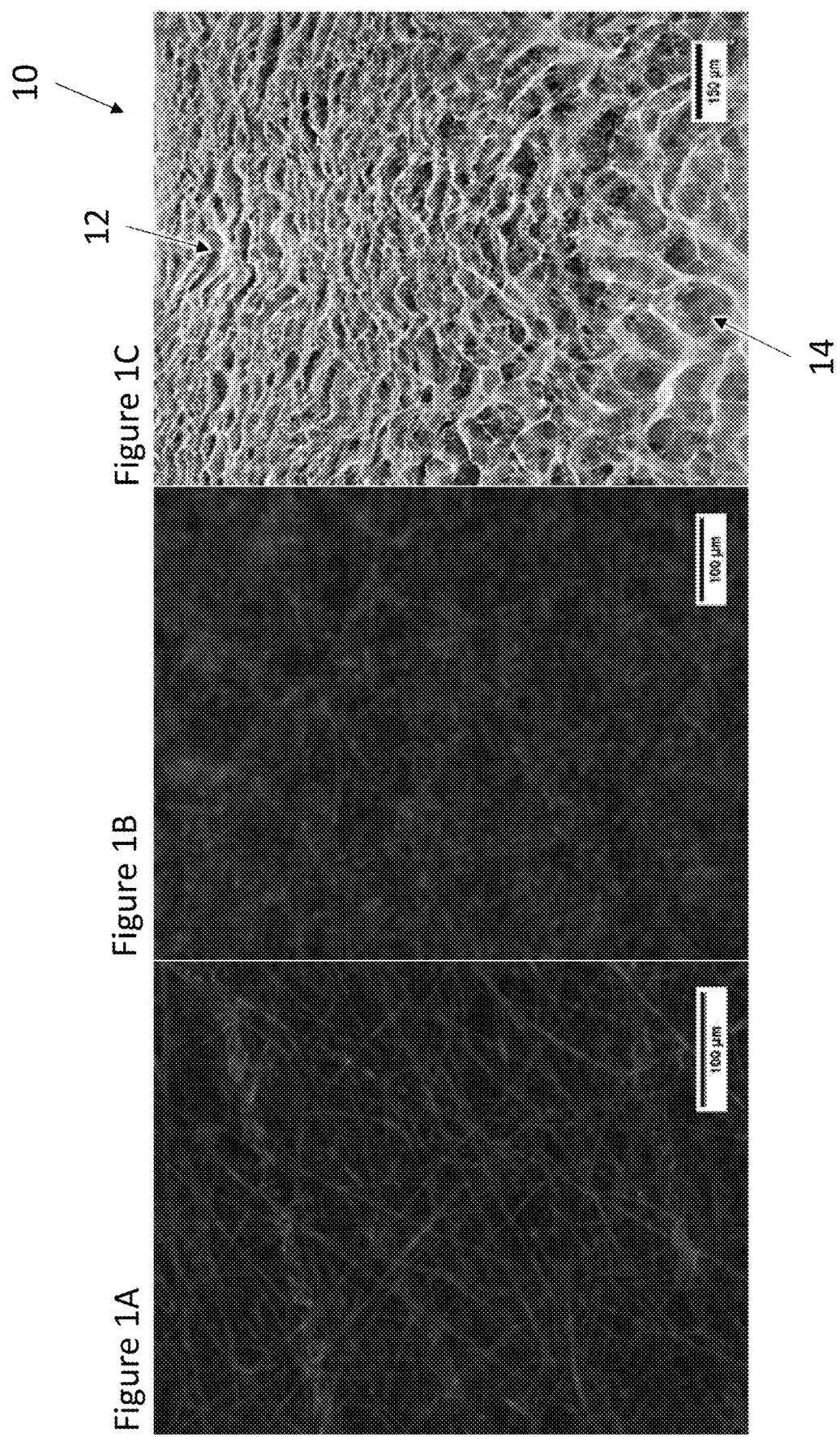
FIG. 1A through FIG. 1C depicts an exemplary scaffold of the present invention before hydration with soy fibers in red (DilC18) and PEO fibers in blue (DiOC18) visible (FIG. 1A), after hydration with only soy fibers visible (FIG. 1B), and after lyophilization (FIG. 1C).

The present invention provides porous biomimetic scaffolds and methods for making the same. The scaffolds have graded pore sizes for enhanced cell penetration. The scaffolds are useful for wound regeneration and tissue modeling by mimicking the inherent stratified structure of certain tissues.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, the exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

As used here, "biocompatible" refers to any material, which, when implanted in a mammal, does not provoke an adverse response in the mammal. A biocompatible material, when introduced into an individual, is not toxic or injurious to that individual, nor does it induce immunological rejection of the material in the mammal.

As used herein, a "culture," refers to the cultivation or growth of cells, for example, tissue cells, in or on a nutrient medium. As is well known to those of skill in the art of cell or tissue culture, a cell culture is generally begun by removing cells or tissue from a human or other animal, dissociating the cells by treating them with an enzyme, and spreading a suspension of the resulting cells out on a flat surface, such as the bottom of a Petri dish. There the cells generally form a thin layer of cells called a "monolayer" by producing glycoprotein-like material that causes the cells to adhere to the plastic or glass of the Petri dish. A layer of culture medium, containing nutrients suitable for cell growth, is then placed on top of the monolayer, and the culture is incubated to promote the growth of the cells.

As used herein, "extracellular matrix composition" includes both soluble and non-soluble fractions or any portion thereof. The non-soluble fraction includes those secreted ECM proteins and biological components that are deposited on the support or scaffold. The soluble fraction includes refers to culture media in which cells have been cultured and into which the cells have secreted active agent(s) and includes those proteins and biological components not deposited on the scaffold. Both fractions may be collected, and optionally further processed, and used individually or in combination in a variety of applications as described herein.

As used herein, a "graft" refers to a cell, tissue, organ, or biomaterial that is implanted into an individual, typically to replace, correct or otherwise overcome a defect. A graft may further comprise a scaffold. The tissue or organ may consist of cells that originate from the same individual; this graft is referred to herein by the following interchangeable terms: "autograft", "autologous transplant", "autologous implant" and "autologous graft". A graft comprising cells from a genetically different individual of the same species is referred to herein by the following interchangeable terms: "allograft," "allogeneic transplant," "allogeneic implant," and "allogeneic graft." A graft from an individual to his identical twin is referred to herein as an "isograft," a "syngeneic transplant," a "syngeneic implant" or a "syngeneic graft." A "xenograft," "xenogeneic transplant," or "xenogeneic implant" refers to a graft from one individual to another of a different species. The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein "growth factors" is intended the following non-limiting factors including, but not limited to, growth hormone, erythropoietin, thrombopoietin, interleukin 3, interleukin 6, interleukin 7, macrophage colony stimulating factor, c-kit ligand/stem cell factor, osteoprotegerin ligand, insulin, insulin like growth factors, epidermal growth factor (EGF), fibroblast growth factor (FGF), nerve growth factor, ciliary neurotrophic factor, platelet derived growth factor (PDGF), transforming growth factor (TGF-beta), hepatocyte growth factor (HGF), and bone morphogenetic protein at concentrations of between picogram/ml to milligram/ml levels.

As used herein, "polymer" includes copolymers. "Copolymers" are polymers formed of more than one polymer precursor. Polymers as used herein include those that are soluble in a solvent and are insoluble in an antisolvent.

As used herein, "scaffold" refers to a structure, comprising a biocompatible material that provides a surface suitable for adherence and proliferation of cells. A scaffold may further provide mechanical stability and support. A scaffold may be in a particular shape or form so as to influence or delimit a three-dimensional shape or form assumed by a population of proliferating cells. Such shapes or forms include, but are not limited to, films (e.g. a form with two-dimensions substantially greater than the third dimension), ribbons, cords, sheets, flat discs, cylinders, spheres, 3-dimensional amorphous shapes, etc.

As used herein, "tissue engineering" refers to the process of generating a tissue ex vivo for use in tissue replacement or reconstruction. Tissue engineering is an example of "regenerative medicine," which encompasses approaches to the repair or replacement of tissues and organs by incorporation of cells, gene or other biological building blocks, along with bioengineered materials and technologies.

As used herein, the terms "tissue grafting" and "tissue reconstructing" both refer to implanting a graft into an individual to treat or alleviate a tissue defect, such as a lung defect or a soft tissue defect.

"Transplant" refers to a biocompatible lattice or a donor tissue, organ or cell, to be transplanted. An example of a transplant may include but is not limited to skin cells or tissue, bone marrow, and solid organs such as heart, pancreas, kidney, lung and liver.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

Scaffolds

The present invention provides fibrous scaffolds having graded pore sizes that facilitate cellular infiltration. The scaffolds are useful for engineering tissues with intrinsic graded architecture, such as skin or bone. The gradient-porous structure mimics the native bio-architecture of the extracellular matrix of these tissues, allowing for more natural, anisotropic cell penetration into the scaffolds and improved cell motility and migration within the construct compared to other porous scaffolds. The size distribution of the pores throughout the scaffolds enhances segregation and arrangement of diverse cell types. For example, dermal fibroblast and keratinocytes can be located in the scaffolds at positions that closely mimic the inherent stratified structure of their respective native tissues. Moreover, the pores allow for efficient transport of bioactive molecules, nutrition factors, and waste products Referring now to FIG. 1A through FIG. 1C, an exemplary scaffold 10 is depicted. Scaffold 10 is a porous material comprising plant protein fibers. The plant proteins can be derived from any suitable plant, such as soy protein isolate, wheat gluten, corn zein, pea protein, and the like. Scaffold 10 is formed to have a first surface 12, a second surface 14, and a thickness therebetween, wherein surface 12 comprises a first average pore size and surface 14 comprises a second pore size. The SPI fibers can have any suitable average diameter, such as between 0.5 µm and 5 µm. In one embodiment, the first average pore size of surface 12 is greater than the second average pore size of surface 14. In another embodiment, the second average pore size of surface 14 is greater than the first average pore size of surface 12. The average pore size for the surface having a smaller average pore size can be between 1 µm and 20 µm, or in one embodiment, between 1 µm and 10 µm. The average pore size for the surface having a greater average pore size can be between 10 µm and 1000 µm, or in one embodiment, between 10 µm and 200 µm. The average pore size increases gradually through scaffold 10 from the surface having the smaller average pore size to the surface having the greater average pore size. In various embodiments, the change in average pore size can be linear or nonlinear. In various embodiments, a plurality of scaffolds 10 may be combined to form a multi-component scaffold having a dynamic average pore size. For example, two scaffolds 10 may be fused surface-to-surface with mirrored gradient orientation to form a thicker scaffold having an average pore size that increases or decreases from the outer surfaces towards the scaffold interior. In another example, two scaffolds 10 may be fused surface-to-surface with the same gradient orientation to form a thicker scaffold having an abrupt transition between large pores and small pores at the surface-to-surface interface.

In certain embodiments, the structure of scaffold 10 can be described in terms of porosity. For example, first surface 12 can have a first porosity and surface 14 can have a second porosity, wherein the first porosity is greater than the second porosity or the second porosity is greater than the first porosity. The porosity of the surface having a lesser porosity can be between 1% and 50%. The porosity of the surface having a greater porosity can be between 50% and 99%. The porosity of scaffold 10 increases gradually from the surface having the lesser porosity to the surface having the greater porosity. The change in porosity can be linear or nonlinear.

In certain embodiments, the structure of scaffold 10 can be described in terms of the number of pores, or pore number. For example, first surface 12 can have a first pore number and surface 14 can have a second pore number, wherein the first pore number is greater than the second pore number or the second pore number is greater than the first pore number. The pore number of scaffold 10 increases gradually from the surface having the smaller pore number to the surface having the greater pore number. The change in pore number can be linear or nonlinear.

Scaffold 10 can have any suitable shape. In some embodiments, scaffold 10 is substantially planar, such as in the form of a sheet. In other embodiments, scaffold 10 can be shaped into a three dimensional structure, such as a tube or a sphere. Scaffold 10 can have any suitable thickness, such as a thickness that is less than 100 µm or as great as several millimeters. In one embodiment, the thickness of biomimetic scaffold is between 500 µm and 5000 µm, or in another embodiment, between 500 µm and 2000 µm. Scaffold 10 can have any geometric shape. In various embodiments, scaffold 10 can be trimmed or sized to accommodate any suitable shape.

In various embodiments, scaffold 10 comprises soy protein isolate (SPI), mitigating the immune response in a host body and reducing and shortening the inflammatory processes that proceed tissue remodeling. The term "soy protein isolate" as used herein is used in the sense conventional to the soy protein industry. For example, a soy protein isolate is a soy material having a protein content of at least 90% soy protein on a moisture free basis. "Isolated soy protein", as used in the art, has the same meaning as "soy protein isolate" as used herein and as used in the art. A soy protein isolate is formed from soybeans by removing the hull and germ of the soybean from the cotyledon, flaking or grinding the cotyledon and removing oil from the flaked or ground cotyledon, separating the soy protein and carbohydrates of the cotyledon from the cotyledon fiber and lipids, and subsequently separating the soy protein from the carbohydrates. In certain embodiments, the resultant material is washed with ethanol to remove a percentage of isoflavonoids. In one embodiment, the soy-based composition comprises a fibrous material containing soy protein and soy cotyledon fiber. The fibrous material generally comprises a defatted soy protein material and soy cotyledon fiber. The fibrous material is produced by extruding the soy protein material and soy cotyledon fiber.

In various embodiments, the scaffolds can be modified with one or more functional groups for covalently attaching a variety of proteins (e.g., collagen) or compounds such as therapeutic agents. Therapeutic agents which may be linked to the scaffold include, but are not limited to, analgesics, anesthetics, antifungals, antibiotics, anti-inflammatories, anthelmintics, antidotes, antiemetics, antihistamines, anticancer drugs, antihypertensives, antimalarials, antimicrobials, antipsychotics, antipyretics, antiseptics, antiarthritics, antituberculotics, antitussives, antivirals, cardioactive drugs, cathartics, chemotherapeutic agents, a colored or fluorescent imaging agent, corticoids (such as steroids), antidepressants, depressants, diagnostic aids, diuretics, enzymes, expectorants, hormones, hypnotics, minerals, nutritional supplements, parasympathomimetics, potassium supplements, radiation sensitizers, a radioisotope, fluorescent nanoparticles such as nanodiamonds, sedatives, sulfonamides, stimulants, sympathomimetics, tranquilizers, urinary anti-infectives, vasoconstrictors, vasodilators, vitamins, xanthine derivatives, and the like. The therapeutic agent may also be other small organic molecules, naturally isolated entities or their analogs, organometallic agents, chelated metals or metal salts, peptide-based drugs, or peptidic or non-peptidic receptor targeting or binding agents. It is contemplated that linkage of the therapeutic agent to the scaffold may be via a protease sensitive linker or other biodegradable linkage. Molecules which may be incorporated into the biomimetic scaffold include, but are not limited to, vitamins and other nutritional supplements; glycoproteins (e.g., collagen); fibronectin; peptides and proteins; carbohydrates (both simple and/or complex); proteoglycans; antigens; oligonucleotides (sense and/or antisense DNA and/or RNA); antibodies (for example, to infectious agents, tumors, drugs or hormones); and gene therapy reagents.

In various embodiments, the scaffolds can further comprise one or more polysaccharide, including glycosaminoglycans (GAGs) or glucosaminoglycans, with suitable viscosity, molecular mass, and other desirable properties. The term "glycosaminoglycan" is intended to encompass any glycan (i.e., polysaccharide) comprising an unbranched polysaccharide chain with a repeating disaccharide unit, one of which is always an amino sugar. These compounds as a class carry a high negative charge, are strongly hydrophilic, and are commonly called mucopolysaccharides. This group of polysaccharides includes heparin, heparan sulfate, chondroitin sulfate, dermatan sulfate, keratan sulfate, and hyaluronic acid. These GAGs are predominantly found on cell surfaces and in the extracellular matrix. The term "glucosaminoglycan" is also intended to encompass any glycan (i.e. polysaccharide) containing predominantly monosaccharide derivatives in which an alcoholic hydroxyl group has been replaced by an amino group or other functional group such as sulfate or phosphate. An example of a glucosaminoglycan is poly-N-acetyl glucosaminoglycan, commonly referred to as chitosan. Exemplary polysaccharides that may be useful in the present invention include dextran, heparan, heparin, hyaluronic acid, alginate, agarose, carageenan, amylopectin, amylose, glycogen, starch, cellulose, chitin, chitosan and various sulfated polysaccharides such as heparan sulfate, chondroitin sulfate, dextran sulfate, dermatan sulfate, or keratan sulfate.

In various embodiments, the scaffolds can further comprise one or more extracellular matrix material and/or blends of naturally occurring extracellular matrix material, including but not limited to collagen, fibrin, fibrinogen, thrombin, elastin, laminin, fibronectin, hyaluronic acid, chondroitin 4-sulfate, chondroitin 6-sulfate, dermatan sulfate, heparin sulfate, heparin, and keratan sulfate, proteoglycans, and combinations thereof. Some collagens that may be beneficial include but are not limited to collagen types I, II, III, IV, V, VI, VII, VIII, IX, X, XI, XII, XIII, XIV, XV, XVI, XVII, XVIII, and XIX. These proteins may be in any form, including but not limited to native and denatured forms. The scaffolds can further comprise one or more carbohydrates such as chitin, chitosan, alginic acids, and alginates such as calcium alginate and sodium alginate. These materials may be isolated from plant products, humans or other organisms or cells or synthetically manufactured. Also contemplated are crude extracts of tissue, extracellular matrix material, or extracts of non-natural tissue, alone or in combination. Extracts of biological materials, including but are not limited to cells, tissues, organs, and tumors may also be included.

In various embodiments, the scaffolds can further comprise one or more synthetic material. The synthetic materials are preferably biologically compatible for administration in vivo or in vitro. Such polymers include but are not limited to the following: poly(urethanes), poly(siloxanes) or silicones, poly(ethylene), poly(vinyl pyrrolidone), poly(2-hydroxy ethyl methacrylate), poly(N-vinyl pyrrolidone), poly (methyl methacrylate), poly(vinyl alcohol), poly(acrylic acid), polyacrylamide, poly(ethylene-co-vinyl acetate), poly (ethylene glycol), poly(methacrylic acid), polylactic acid (PLA), polyglycolic acids (PGA), poly(lactide-co-glycolides) (PLGA), nylons, polyamides, polyanhydrides, poly (ethylene-co-vinyl alcohol) (EVOH), polycaprolactone, poly(vinyl acetate) (PVA), polyvinylhydroxide, poly(ethylene oxide) (PEO) and polyorthoesters or any other similar synthetic polymers that may be developed that are biologically compatible. Polymers with cationic moieties can also be used, such as poly(allyl amine), poly(ethylene imine), poly(lysine), and poly(arginine). The polymers may have any molecular structure including, but not limited to, linear, branched, graft, block, star, comb, and dendrimer structures.

In one embodiment, the scaffolds can further comprise one or more natural or synthetic drug, such as nonsteroidal anti-inflammatory drugs (NSAIDs). In one embodiment, the scaffolds can further comprise antibiotics, such as penicillin. In one embodiment, the scaffolds can further comprise natural peptides, such as glycyl-arginyl-glycyl-aspartyl-serine (GRGDS), arginylglycylaspartic acid (RGD), and amelogenin. In one embodiment, the scaffolds can further comprise proteins, such as chitosan and silk. In one embodiment, the scaffolds can further comprise sucrose, fructose, cellulose, or mannitol. In one embodiment, the scaffolds can further comprise extracellular matrix proteins, such as fibronectin, vitronectin, laminin, collagens, and vixapatin (VP12). In one embodiment, the scaffolds can further comprise disintegrins, such as VLO4. In one embodiment, the scaffolds can further comprise decellularized or demineralized tissue. In one embodiment, the scaffolds can further comprise synthetic peptides, such as emdogain. In one embodiment, the scaffolds can further comprise nutrients, such as bovine serum albumin. In one embodiment, the scaffolds can further comprise vitamins, such as vitamin B2, vitamin Ad, Vitamin D, Vitamin E, and Vitamin K. In one embodiment, the scaffold can further comprise nucleic acids, such as mRNA and DNA. In one embodiment, the scaffolds can further comprise natural or synthetic steroids and hormones, such as dexamethasone, hydrocortisone, estrogens, and its derivatives. In one embodiment, the scaffold can further comprise growth factors, such as fibroblast growth factor (FGF), transforming growth factor beta (TGF-$\beta$), and epidermal growth factor (EGF). In one embodiment, the scaffolds can further comprise a delivery vehicle, such as nanoparticles, microparticles, liposomes, viral and non-viral transfection systems.

In one embodiment, the scaffolds are provided cell-free. In another embodiment, the scaffolds are provided pre-seeded with one or more populations of cells to form an artificial tissue construct. The artificial tissue construct may be autologous, where the cell populations are derived from a patient's own tissue, or allogenic, where the cell populations are derived from another subject within the same species as the patient. The artificial organ construct may also be xenogenic, where the different cell populations are derived form a mammalian species that is different from the subject. For example the cells may be derived from organs of mammals such as humans, monkeys, dogs, cats, mice, rats, cows, horses, pigs, goats and sheep.

Cells may be isolated from a number of sources, including, for example, biopsies from living subjects and whole-organ recover from cadavers. The isolated cells are preferably autologous cells, obtained by biopsy from the subject intended to be the recipient. The biopsy may be obtained using a biopsy needle, a rapid action needle which makes the procedure quick and simple.

Cells may be isolated using techniques known to those skilled in the art. For example, the tissue may be disaggregated mechanically and/or treated with digestive enzymes and/or chelating agents that weaken the connections between neighboring cells making it possible to disperse the tissue into a suspension of individual cells without appreciable cell breakage. Enzymatic dissociation may be accomplished by mincing the tissue and treating the minced tissue with any of a number of digestive enzymes either alone or in combination. These include but are not limited to trypsin, chymotrypsin, collagenase, elastase, and/or hyaluronidase, DNase, pronase and dispase. Mechanical disruption may also be accomplished by a number of methods including, but not limited to, scraping the surface of the tissue, the use of grinders, blenders, sieves, homogenizers, pressure cells, or sonicators.

Once the tissue has been reduced to a suspension of individual cells, the suspension may be fractionated into subpopulations from which the cells elements may be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counterstreaming centrifugation), unit gravity separation, countercurrent distribution, electrophoresis and fluorescence-activated cell sorting.

Cell fractionation may also be desirable, for example, when the donor has diseases such as cancer or metastasis of other tumors to the desired tissue. A cell population may be sorted to separate malignant cells or other tumor cells from normal noncancerous cells. The normal noncancerous cells, isolated from one or more sorting techniques, may then be used for tissue reconstruction.

Isolated cells may be cultured in vitro to increase the number of cells available for seeding the biomimetic scaffold. The use of allogenic cells, and more preferably autologous cells, is preferred to prevent tissue rejection. However, if an immunological response does occur in the subject after implantation of the artificial organ, the subject may be treated with immunosuppressive agents such as cyclosporin or FK506 to reduce the likelihood of rejection. In certain embodiments, chimeric cells, or cells from a transgenic animal, may be seeded onto the biocompatible scaffold.

Isolated cells may be transfected prior to coating with genetic material. Useful genetic material may be, for example, genetic sequences which are capable of reducing or eliminating an immune response in the host. For example, the expression of cell surface antigens such as class I and class II histocompatibility antigens may be suppressed. This may allow the transplanted cells to have reduced chances of rejection by the host. In addition, transfection could also be used for gene delivery.

Isolated cells may be normal or genetically engineered to provide additional or normal function. Methods for genetically engineering cells with retroviral vectors, polyethylene glycol, or other methods known to those skilled in the art may be used. These include using expression vectors which transport and express nucleic acid molecules in the cells. (See Goeddel; Gene Expression Technology: Methods in Enzymology 185, Academic Press, San Diego, Calif. (1990). Vector DNA may be introduced into prokaryotic or cells via conventional transformation or transfection techniques. Suitable methods for transforming or transfecting host cells can be found in Sambrook et al. (Molecular Cloning: A Laboratory Manual, 3nd Edition, Cold Spring Harbor Laboratory press (2001)), and other laboratory textbooks.

Seeding of cells onto the scaffold may be performed according to standard methods. For example, the seeding of cells onto polymeric substrates for use in tissue repair has been reported (see, e.g., Atala, A. et al., J. Urol. 148(2 Pt 2): 658-62 (1992); Atala, A., et al. J. Urol. 150 (2 Pt 2): 608-12 (1993)). Cells grown in culture may be trypsinized to separate the cells, and the separated cells may be seeded on the scaffold. Alternatively, cells obtained from cell culture may be lifted from a culture plate as a cell layer, and the cell layer may be directly seeded onto the scaffold without prior separation of the cells.

In one embodiment, a range of 1 million to 50 million cells are suspended in medium and applied to each square centimeter of a surface of a scaffold. The scaffold is incubated under standard culturing conditions, such as, for example, 37° C. 5% $CO_2$, for a period of time until the cells become attached. However, it will be appreciated that the density of cells seeded onto the scaffold may be varied. For example, greater cell densities promote greater tissue regeneration by the seeded cells, while lesser densities may permit relatively greater regeneration of tissue by cells infiltrating the graft from the host. Other seeding techniques may also be used depending on the matrix or scaffold and the cells. For example, the cells may be applied to the matrix or scaffold by vacuum filtration. Selection of cell types, and seeding of cells onto a scaffold, will be routine to one of ordinary skill in the art in light of the teachings herein.

In one embodiment, the scaffold is seeded with one population of cells to form an artificial tissue construct. In another embodiment, the scaffold is seeded on two sides with two different populations of cells. This may be performed by first seeding one side of the scaffold and then seeding the other side. For example, the scaffold may be placed with one side on top and seeded. The scaffold may then be repositioned so that a second side is on top. The second side may then be seeded with a second population of cells. Alternatively, both sides of the scaffold may be seeded at the same time. For example, two cell chambers may be positioned on both sides (i.e., a sandwich) of the scaffold. The two chambers may be filled with different cell populations to seed both sides of the scaffold simultaneously. The sandwiched scaffold may be rotated, or flipped frequently to allow equal attachment opportunity for both cell populations.

In another embodiment, two separate scaffolds may be seeded with different cell populations. After seeding, the two scaffolds may be attached together to form a single scaffold with two different cell populations on the two sides. Attachment of the scaffolds to each other may be performed using standard procedures such as fibrin glue, liquid co-polymers, sutures, and the like.

In order to facilitate cell growth on the scaffold of the present invention, the scaffold may be coated with one or more cell adhesion-enhancing agents. These agents include but are not limited to collagen, laminin, and fibronectin. The scaffold may also contain cells cultured on the scaffold to form a target tissue substitute. In the alternative, other cells may be cultured on the scaffold of the present invention.

Methods of Fabrication

The invention also relates to methods of making the scaffolds of the present invention. The methods combine electroprocessing with post-processing steps of hydrating the electroprocessed scaffold, freezing the soaked construct, and lyophilizing it. This method produces a hydrated and lyophilized scaffold, which in combination with a sacrificial material, produces the uniquely graded porous scaffolds of the present invention.

Figure 2:
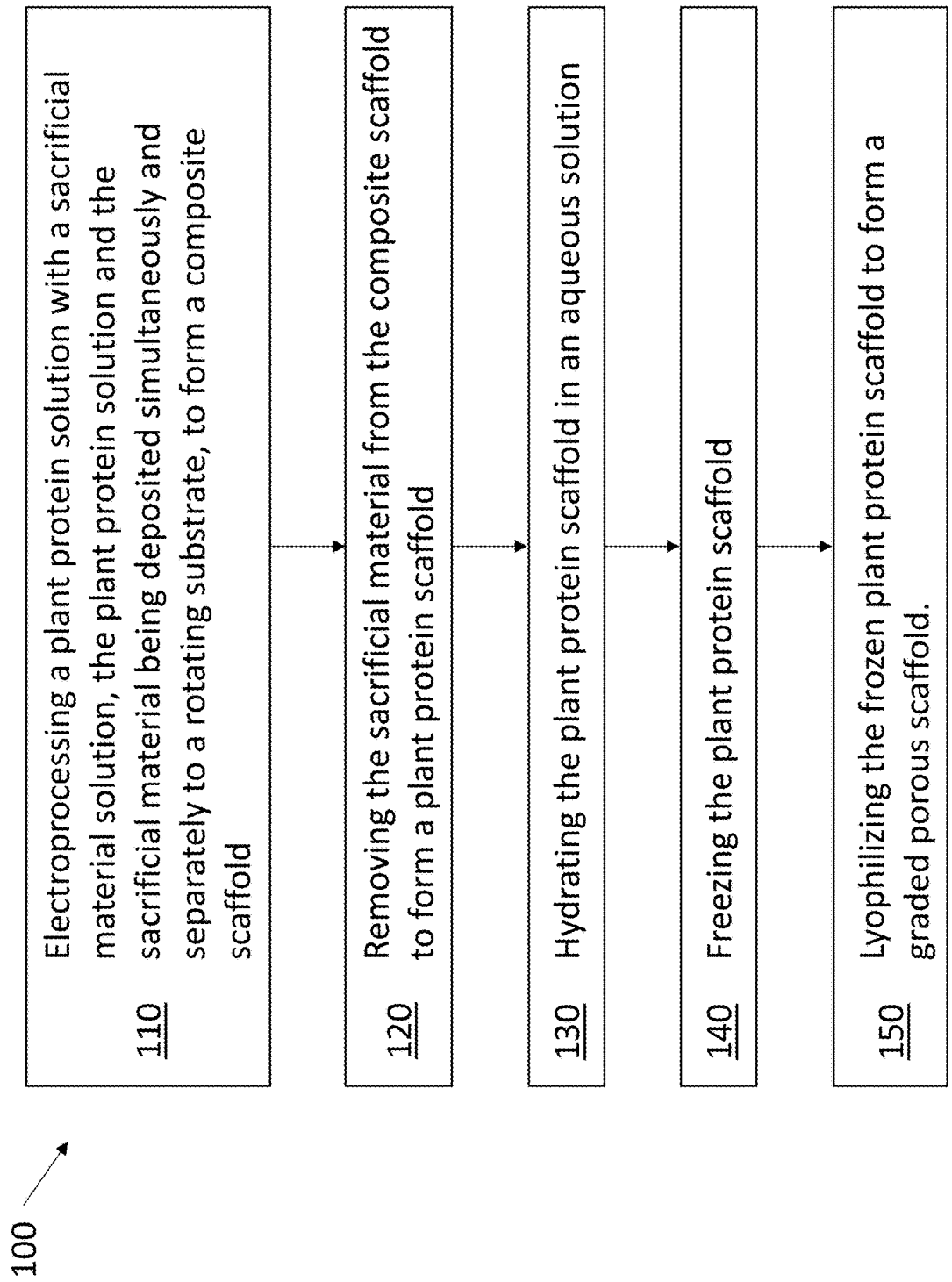
FIG. 2 depicts an exemplary method for fabricating the scaffolds of the present invention.

Referring now to FIG. 2, an exemplary method 100 of making a graded porous scaffold is depicted. Method 100 begins with step 110, wherein a plant protein solution is electroprocessed with a sacrificial material to form a composite scaffold. It is important to note that the plant protein solution and the sacrificial material are simultaneously, yet separately, electrically deposited onto the same rotating substrate. In certain embodiments, the plant protein solution and the sacrificial materials are deposited such that the trajectories of the plant protein solution and sacrificial material deposition are oriented 90 degrees to each other. In step 120, the sacrificial material is removed from the composite scaffold to leave behind a plant protein scaffold. In step 130, the plant protein scaffold is hydrated in an aqueous solution. In step 140, the plant protein scaffold is frozen after being removed from the aqueous solution. In step 150, the frozen plant protein scaffold is lyophilized to form a graded porous scaffold. Lyophilization can be performed at −60° C. and 0.08 mbar.

The SPI solution can prepared in any suitable manner. For example, the SPI solution can comprise SPI dissolved in a 1,1,1,3,3,3,-Hexafluoro-2-propanol (HFP) solution. In some embodiments, the SPI solution can include an amount of the sacrificial material. In one embodiment, the SPI solution comprises 7% (w/v) of SPI and 0.05% (w/v) polyethylene oxide (PEO) dissolved in HFP.

The sacrificial material solution can be prepared in any suitable manner. In certain embodiments, the sacrificial material is water soluble, such that step 120 and step 130 are performed simultaneously (sacrificial fibers are removed during the hydration step). In one embodiment, the sacrificial material comprises 3% (w/v) PEO are dissolved in 90% ethanol. In other embodiments, the sacrificial material can comprise polyethylene oxide, polyvinyl alcohol, or Dextran.

In one embodiment, the electroprocessing is electrospinning. The conditions under which the SPI solution and the sacrificial material solution are co-spun can be performed within any suitable range, such as those disclosed herein. For example, the electric field used in the electrospinning process can be in the range of about 5 to about 50 kV, more preferably from about 10 to about 30 kV. The feed rate of the spinning solutions to the spinneret can be in the range of about 0.1 to about 3 mL/hour, more preferably about 0.5 to about 1.5 mL/hour. The spinnerets can individually or both be supplemented with one or more additional air jet. The spinnerets can be the same distance from the rotating substrate, or they can be at different distances for the SPI solution and the sacrificial material solution.

Persons skilled in the art will understand that the rotating substrate typically involves a mandrel mechanically attached to a motor, often through a drill chuck. In various embodiments, the motor rotates the mandrel at a speed of between about 1 revolution per minute (rpm) to about 40,000 rpm. In one exemplary embodiment, the motor rotation speed of between about 1000 rpm to about 4000 rpm. In another exemplary embodiment, the motor rotation speed of between about 1 rpm to about 300 rpm.

In some embodiments, the SPI solution, the sacrificial solution, or both may further comprise an additional polymer. Non-limiting examples of polymers include: polyurethane, polysiloxane or silicone, polyethylene, polyvinyl pyrrolidone (PVP), poly(2-hydroxy ethyl methacrylate), poly (N-vinyl pyrrolidone), polymethyl methacrylate, polyvinyl alcohol (PVA), polyacrylic acid, polyacrylamide, polyethylene-co-vinyl acetate, polyethylene glycol (PEG), polyethylene oxide (PEO), polymethacrylic acid, polylactide (PLA), polyglycolide (PGA), poly(lactic-co-glycolic acid) (PLGA), polystyrene, polyanhydride, polyorthoester, polycarbonate, and the like.

In some embodiments, the SPI solution, the sacrificial solution, or both may further comprise an additional therapeutic. Non-limiting examples of therapeutics include: anesthetics, antiallergics, antihistamines, antipruritics, muscle relaxants, analgesics, antipyretics, vitamins, antimicrobial agents, antiseptics, disinfectants, fungicides, ectoparasiticides, antiparasitics, alkaloids, salts, ions, anti-inflammatories, wound healing agents, plant extracts, growth factors, polycarbonates, extracellular matrix (ECM) constituents such as ECM proteins, emollients, antibacterial or antiviral agents, tranquilizers, antitussives, nanoparticles such as silver ions, cells such as stem cells, epithelial cells, endothelial cells, and the like.

In some embodiments, the SPI solution, the sacrificial solution, or both may further comprise an additional animal or plant protein. Non-limiting examples include: gelatin, Matrigel, keratin, collagen, elastin, fibrin, hyaluronic acid, glycosaminoglycan, proteoglycan, fibronectin, vitronectin, laminin, chitosan, and soy-chitosan.

Kits of the Invention

The invention also includes a kit comprising components useful within the methods of the invention and instructional material that describes, for instance, the method of using the scaffolds. The kit may comprise components and materials useful for performing the methods of the invention. For instance, the kit may comprise SPI and sacrificial material spinning solutions. In certain embodiments, the kit may comprise preformed scaffolds. In other embodiments, the kit further comprises cell cultures and surgical instruments.

In one embodiment, the kit is for wound treatment. For example, the kit may comprise scaffolds having preset sizes, such as small, medium, large, and extra-large, wherein an operator may select an appropriate kit having an appropriately sized scaffold to fit in a wound. The kit may further comprise bandages, antibiotics, or other drugs to enhance wound regeneration.

In some embodiments, the kit may further comprise scaffolds placed in a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea, and combinations thereof. In one embodiment, the preservative is a combination of about 0.5% to 2.0% benzyl alcohol and 0.05% to 0.5% sorbic acid.

In certain embodiments, the kit comprises instructional material. Instructional material may include a publication, a recording, a diagram, or any other medium of expression which can be used to communicate the usefulness of the device or implant kit described herein. The instructional material of the kit of the invention may, for example, be affixed to a package which contains one or more instruments which may be necessary for the desired procedure. Alternatively, the instructional material may be shipped separately from the package, or may be accessible electronically via a communications network, such as the Internet.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the exemplary embodiments of the present invention, and are not to be construed as limiting in any way the remainder of the disclosure.

Example 1

Graded Hydrated Lyophilized (GHL) Scaffolds

The goal of the present study was to develop fibrous scaffolds with pores large enough to allow cell penetration into the depth of the scaffold, which reportedly initiates/favors the phenotypic switch of macrophages into the tissue remodeling M2 phenotype and thus enhances regenerative wound healing (Garg K et al., Biomaterials 34.18 (2013): 4439-4451; Wang Z et al., Biomaterials 35.22 (2014): 5700-5710; Sussman E M et al., Annals of biomedical engineering 42.7 (2014): 1508-1516).

The main component of the fibrous scaffolds is purified soy protein isolate (SPI), a paradigmatic, biocompatible biomaterial that has been shown to allow attachment, spreading and proliferation of cells in vitro (Lin L et al., Journal of tissue engineering and regenerative medicine 7.12 (2013): 994-1008). The sacrificial component of the scaffold is polyethylene oxide (PEO), an inexpensive polymer compound, readily available and soluble in water. As for the spinning solutions, 7% (w/v) of SPI plus 0.05% (w/v) polyethylene oxide (PEO) were dissolved in 1,1,1,3,3,3,-Hexafluoro-2-propanol (HFP) and, for PEO spinning solution, 3% (w/v) PEO were dissolved in 90% ethanol. The two components were co-electrospun and the resultant scaffold underwent post-processing. During the hydration step, PEO is removed; the lyophilization step yields the graded porosity.

Figure 3:
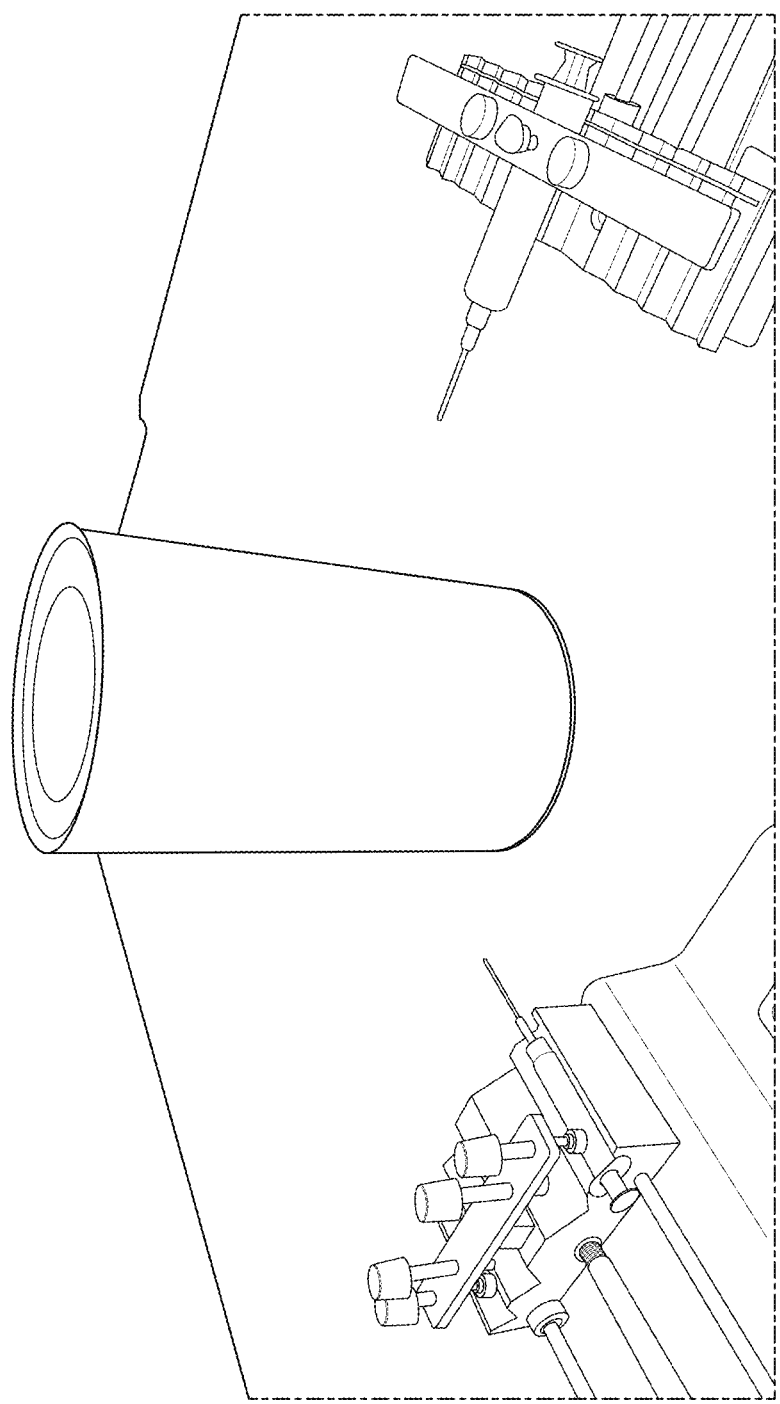
FIG. 3 depicts an experimental setup for fabricating a composite soy protein isolate (SPI) and polyethylene oxide (PEO) scaffold.
Figures 4A, 4B:
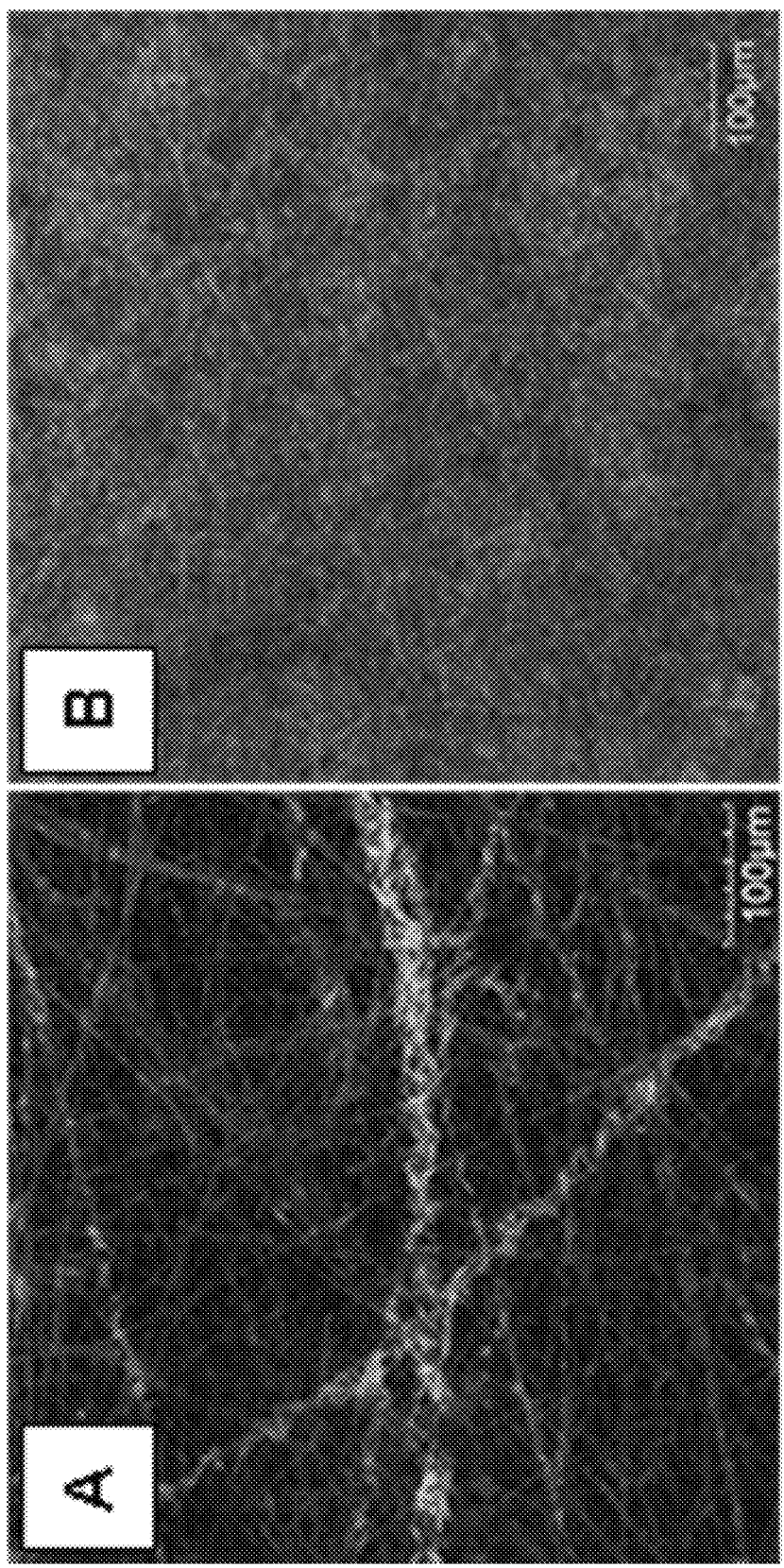
FIG. 4A and FIG. 4B depict an experimental SPI-PEO scaffold before (FIG. 4A) and after (FIG. 4B) hydration for 24 hours in water at 40° C. SPI fibers in red stained with DilC18 and sacrificial PEO fibers in green stained with DiOC18.
Figure 6A:
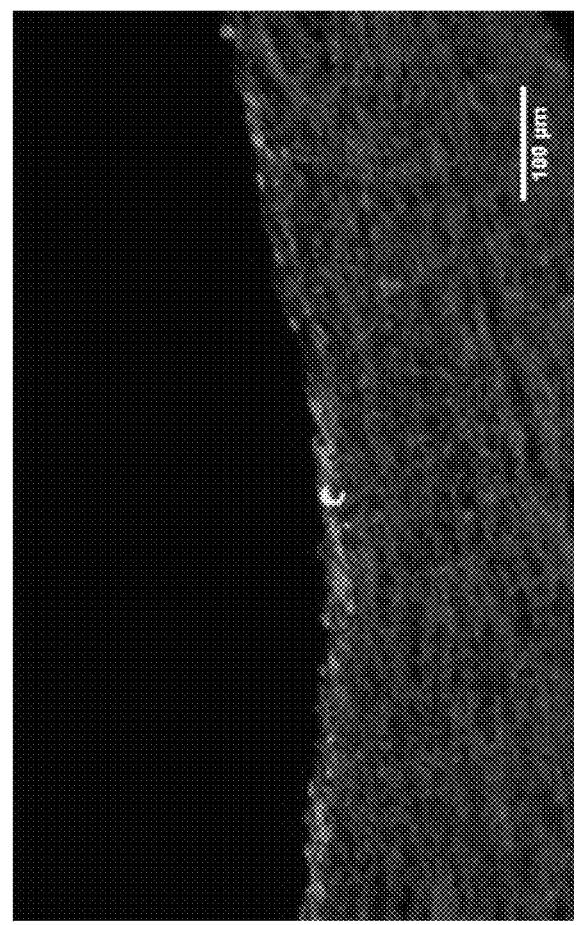
FIG. 6A and FIG. 6B depict the results of experiments demonstrating HDFB cell penetration into a GHL scaffold (FIG. 6A) and a regularly spun SPI scaffold (FIG. 6B) 7 days post seeding.
Figure 6B:
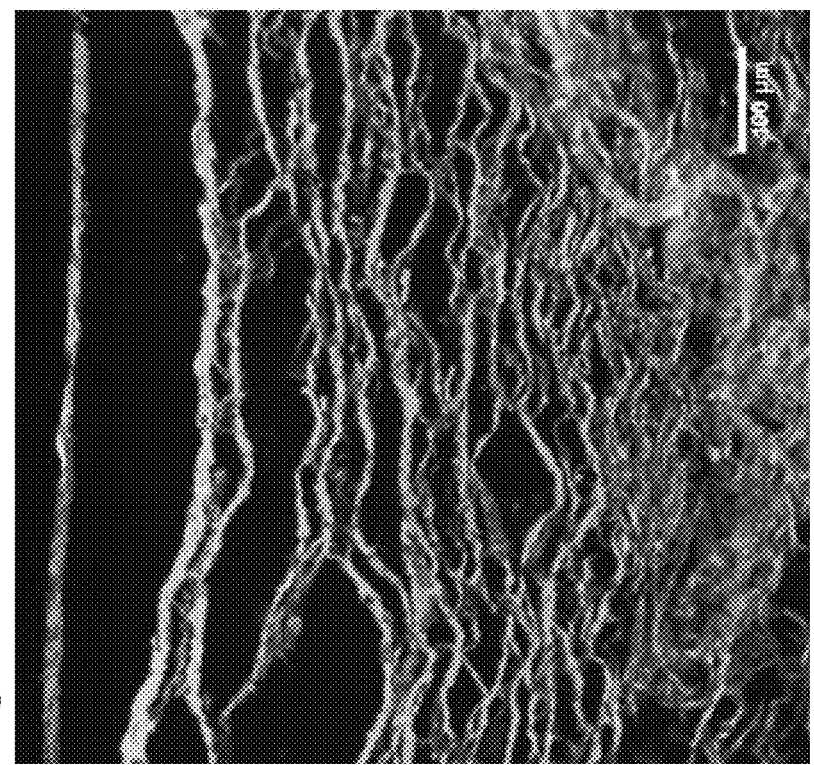

Specifically, the co-spinning system was set up with separate SPI and PEO spinnerets both connected to a high voltage electrostatic field of 13 kV. The PEO spinneret was connected to an additional air jet operated at 1 bar pressure. A vertical rotating mandrel was used to collect the fibers. The two nozzles were arranged 90 degrees to each other and perpendicular to the mandrel (FIG. 3). This arrangement creates a fibrous scaffold containing large fibers of PEO (~20 µm in diameter) and small fibers of SPI (~1.2 µm in diameter). In order to remove the sacrificial fibers from the composite SPI/PEO scaffolds, the scaffolds were immersed in water (40° C.) overnight (FIG. 4A, FIG. 4B). The soaked scaffolds were then transferred to −80° C. for 2 hours. The frozen samples were lyophilized overnight at −60° C. and 0.08 mbar. Cross sections of the resulting GHL scaffold and regularly spun SPI are presented in FIG. 5A and FIG. 5B, respectively. For regularly spun SPI scaffold, 7% (w/v) of SPI plus 0.05% (w/v) polyethylene oxide (PEO) were dissolved in 1,1,1,3,3,3-Hexafluoro-2-propanol (HFP) and electrospun onto a stationary rectangular aluminum target. Electrospinning was conducted at the high voltage electrostatic field of 13 kV and with the spinneret to the aluminum target distance of 15 cm.

In vitro cell studies revealed significant improvement in penetrability of our newly developed scaffold as compared to regularly electrospun SPI scaffolds (FIG. 6A, FIG. 6B, FIG. 7A, FIG. 7B). Animal studies with Sprague Dawley rats were conducted to compare inflammatory responses of GHL scaffolds would affect versus those elicited by conventionally elecrospun SPI scaffolds. Two subcutaneous pouches, one each on the right and left side of the lower dorsal area, were created and a square 10 mm×10 mm scaffold was inserted in each. One was a GHL scaffold and the other one was a conventional spun SPI control. The animals were euthanized 3, 7, and 10 days after the surgery and the tissues surrounding the scaffolds were harvested and prepared for histology.

Figure 8A:
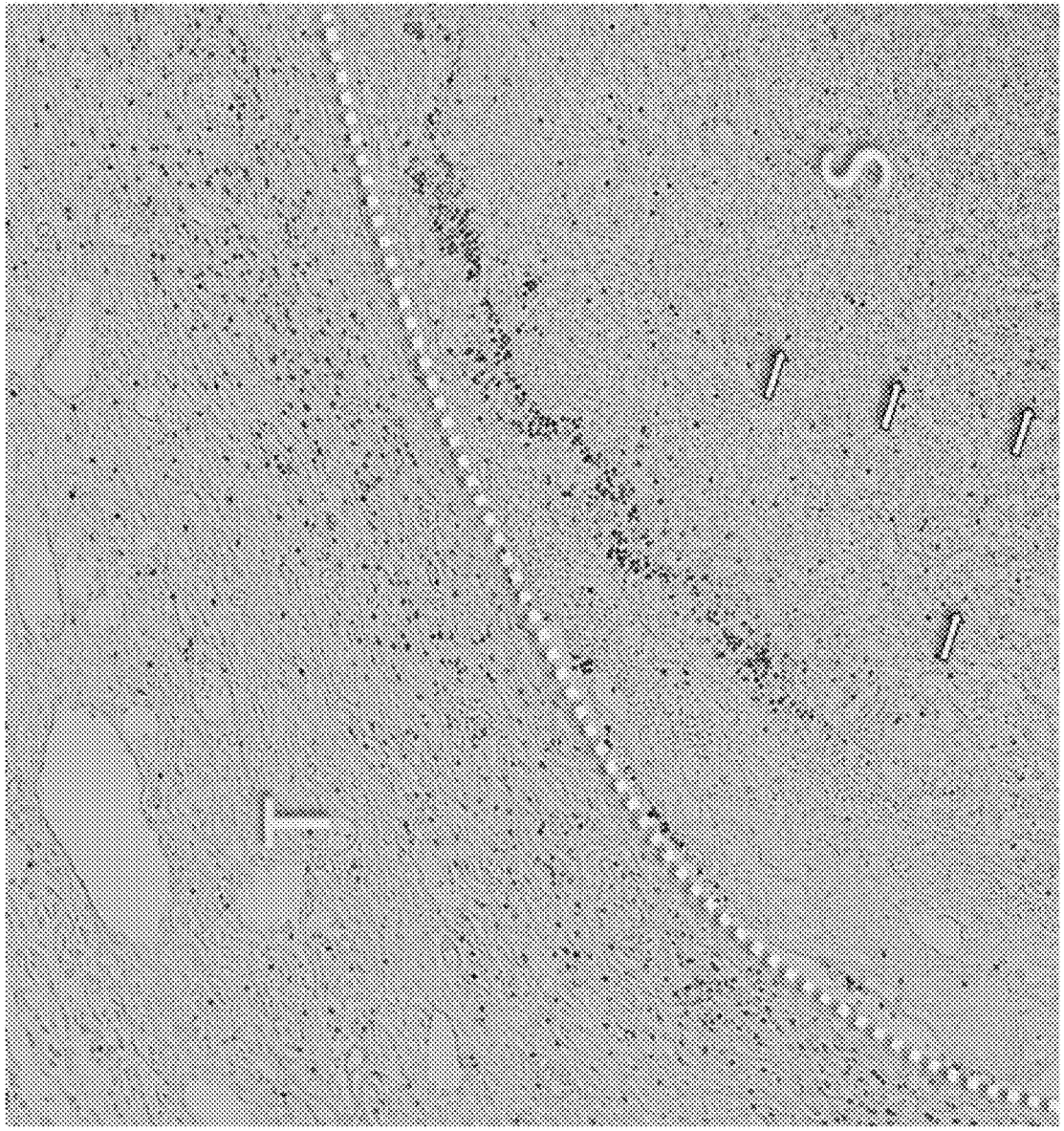
FIG. 8A and FIG. 8B depict IHC staining with pan-macrophages (L1) antibody seven days post-surgery for an HL scaffold showing cell penetration into the inner layers (FIG. 8A, arrows) and a regularly spun scaffold showing minimal cell penetration (FIG. 8B). T is tissue, S is scaffold. The dotted lines indicate the scaffold-tissue border.
Figure 8B:
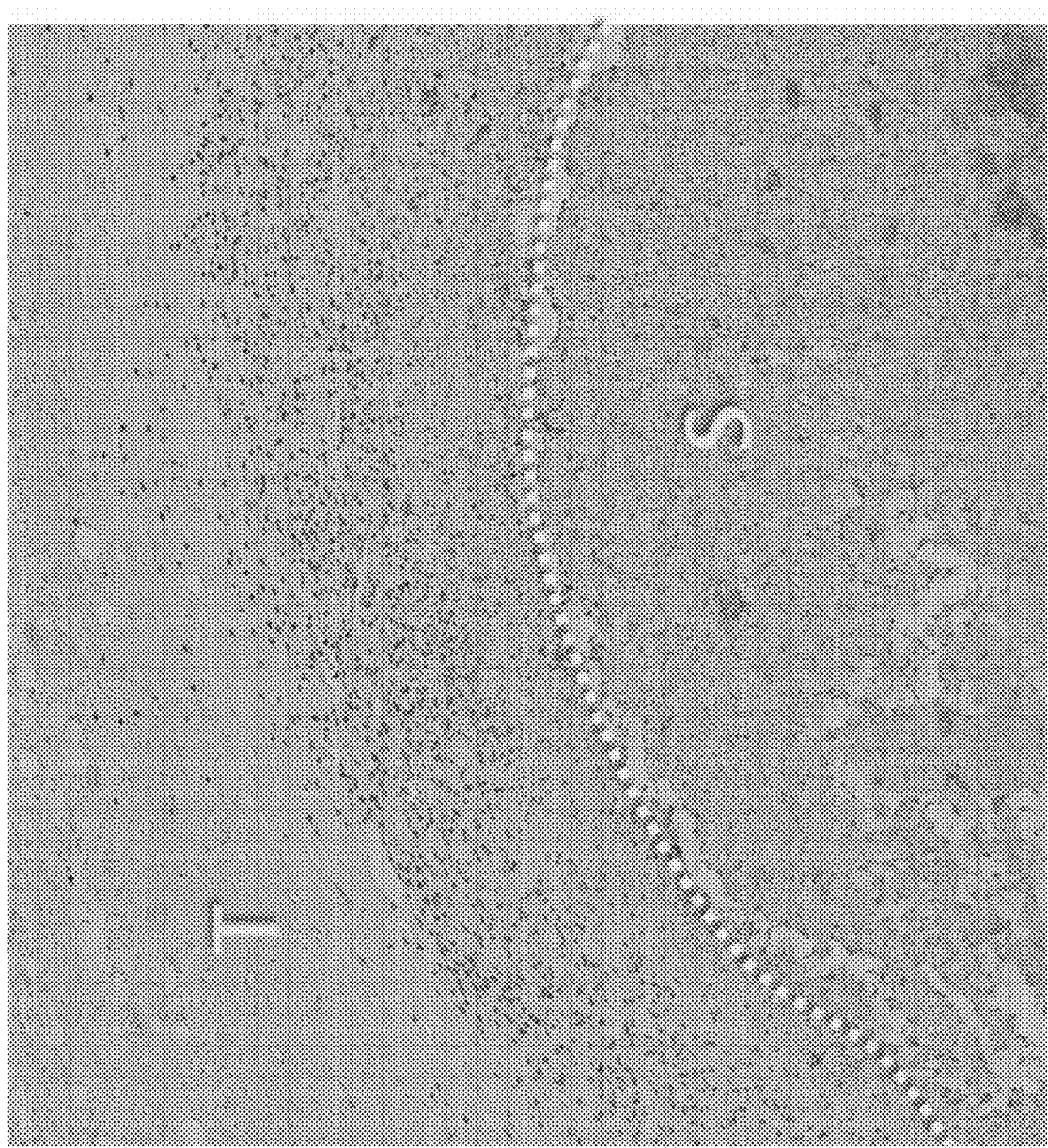
Figure 9:
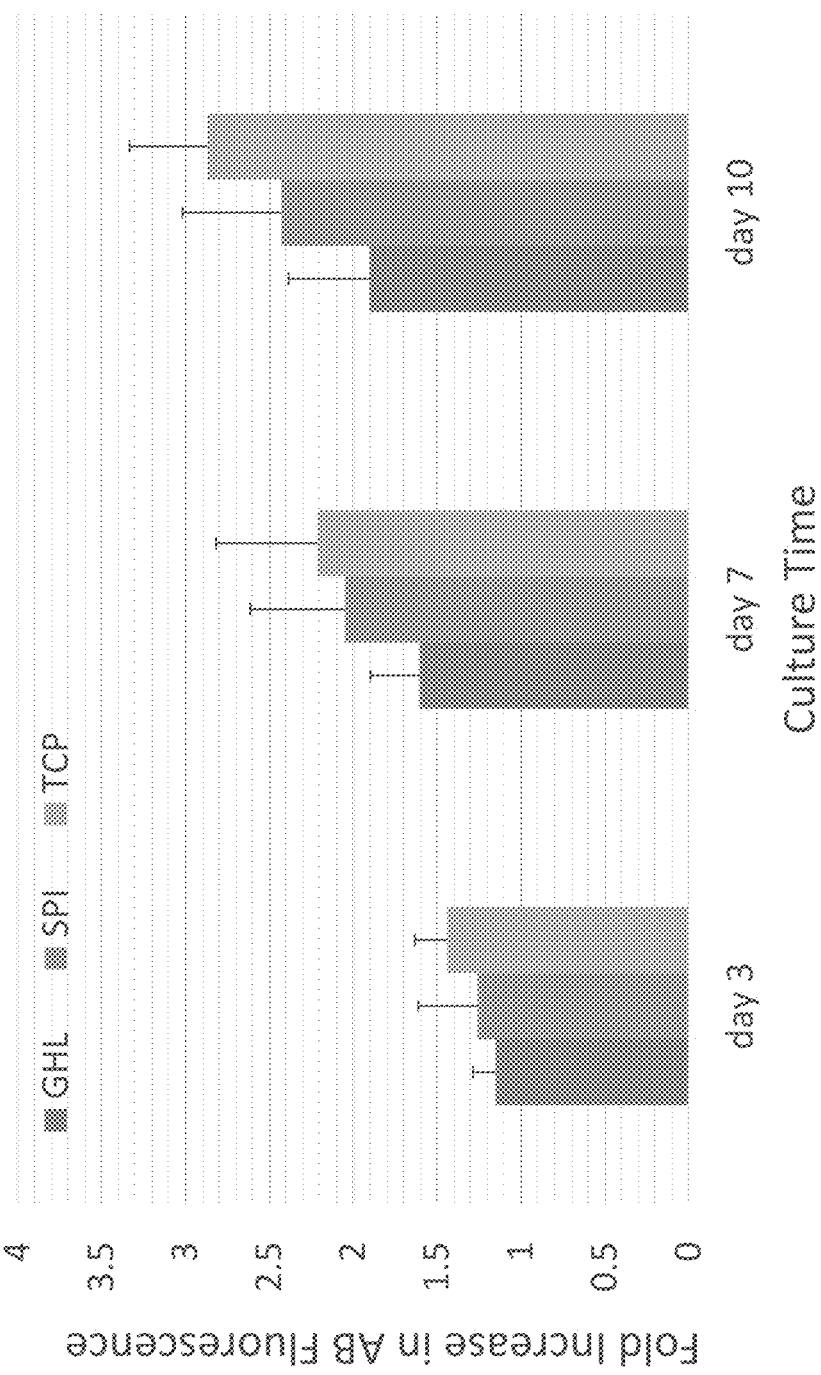
FIG. 9 depicts the results of an alamarBlue assay showing viability of cells on days 3, 7, and 10 post-seeding onto a GHL scaffold.
Figure 11:
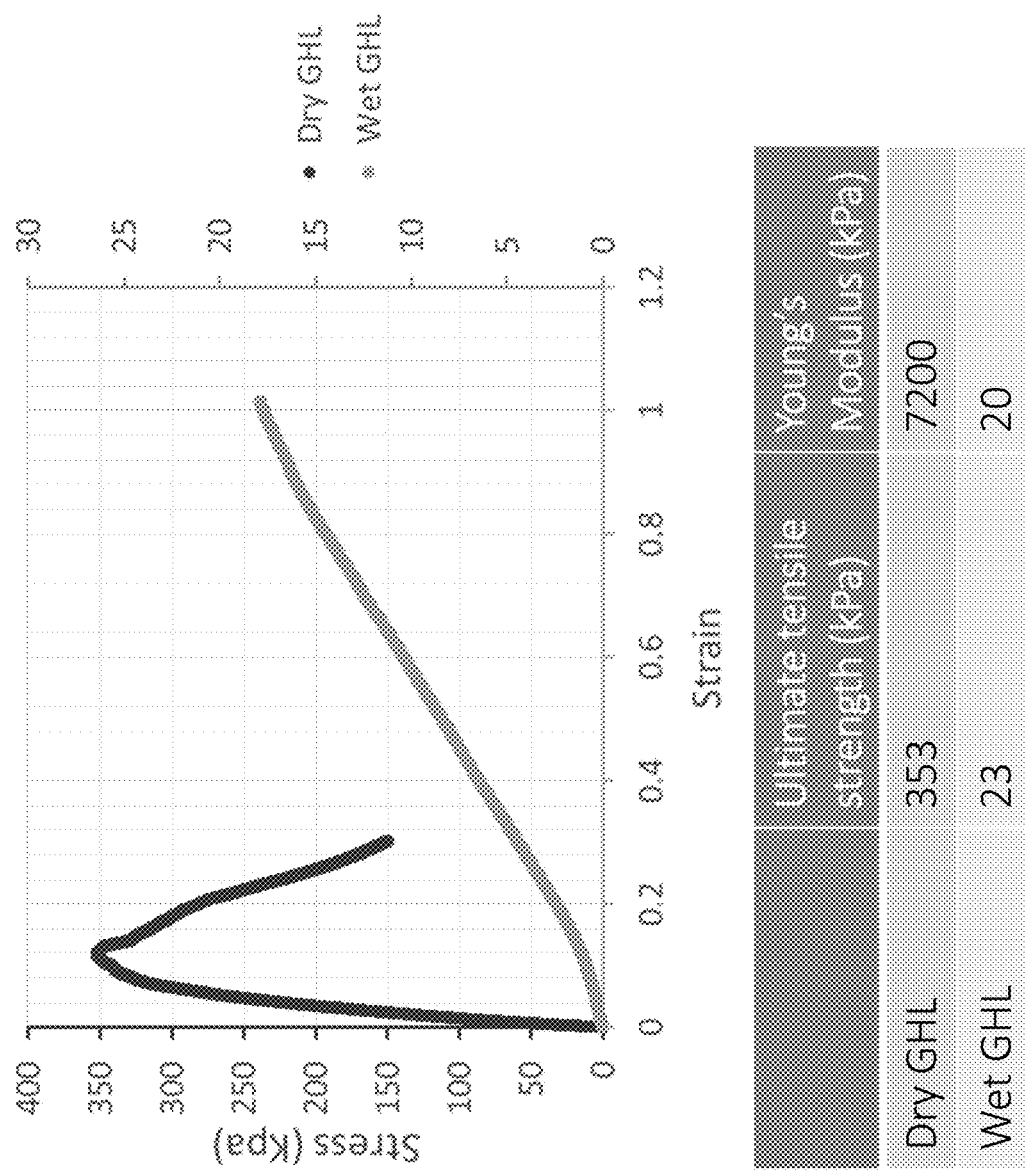
FIG. 11 depicts stress-strain curves from tensile testing of GHL scaffold under wet and dry conditions.
Figure 12C:
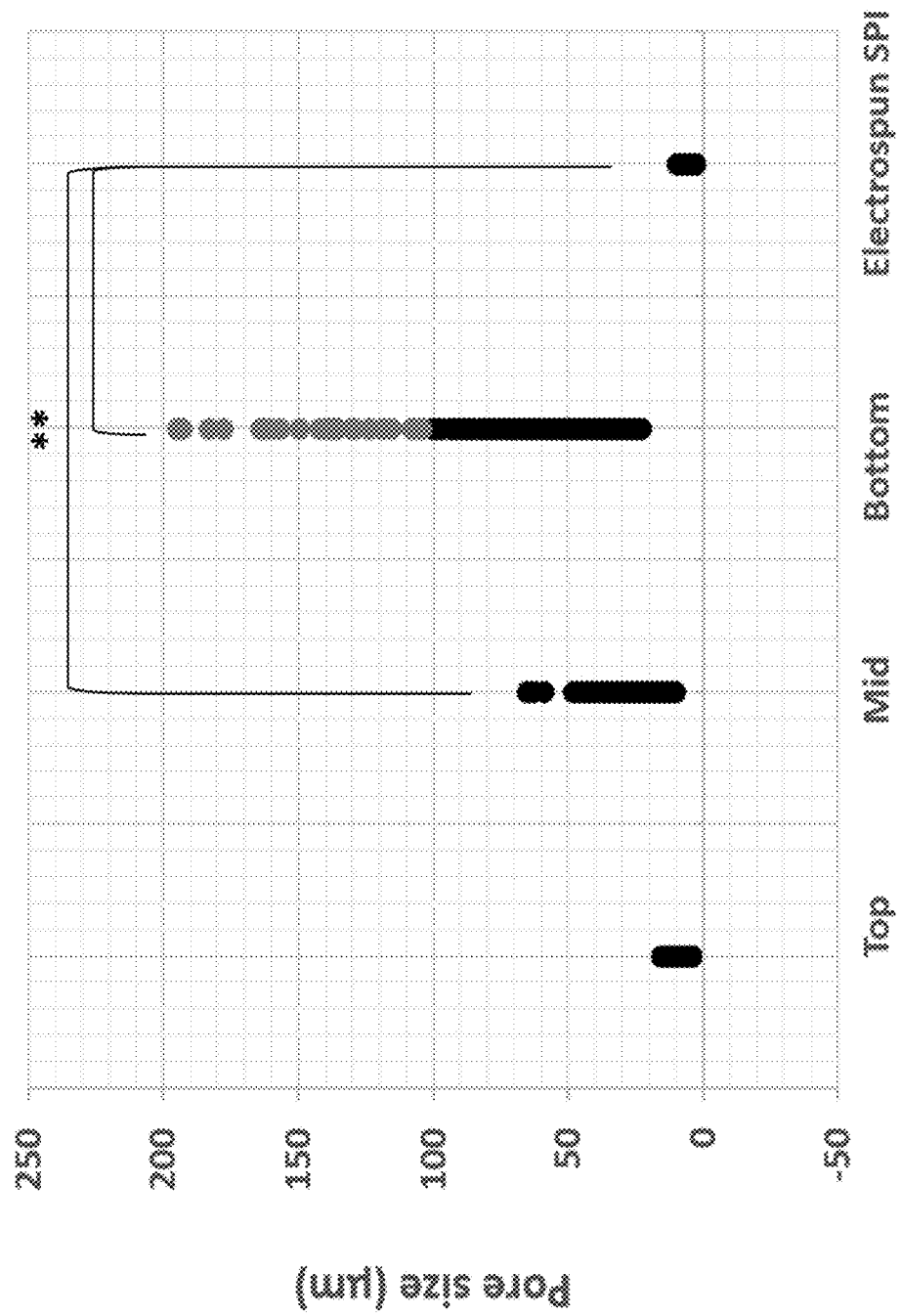
Figure 13:
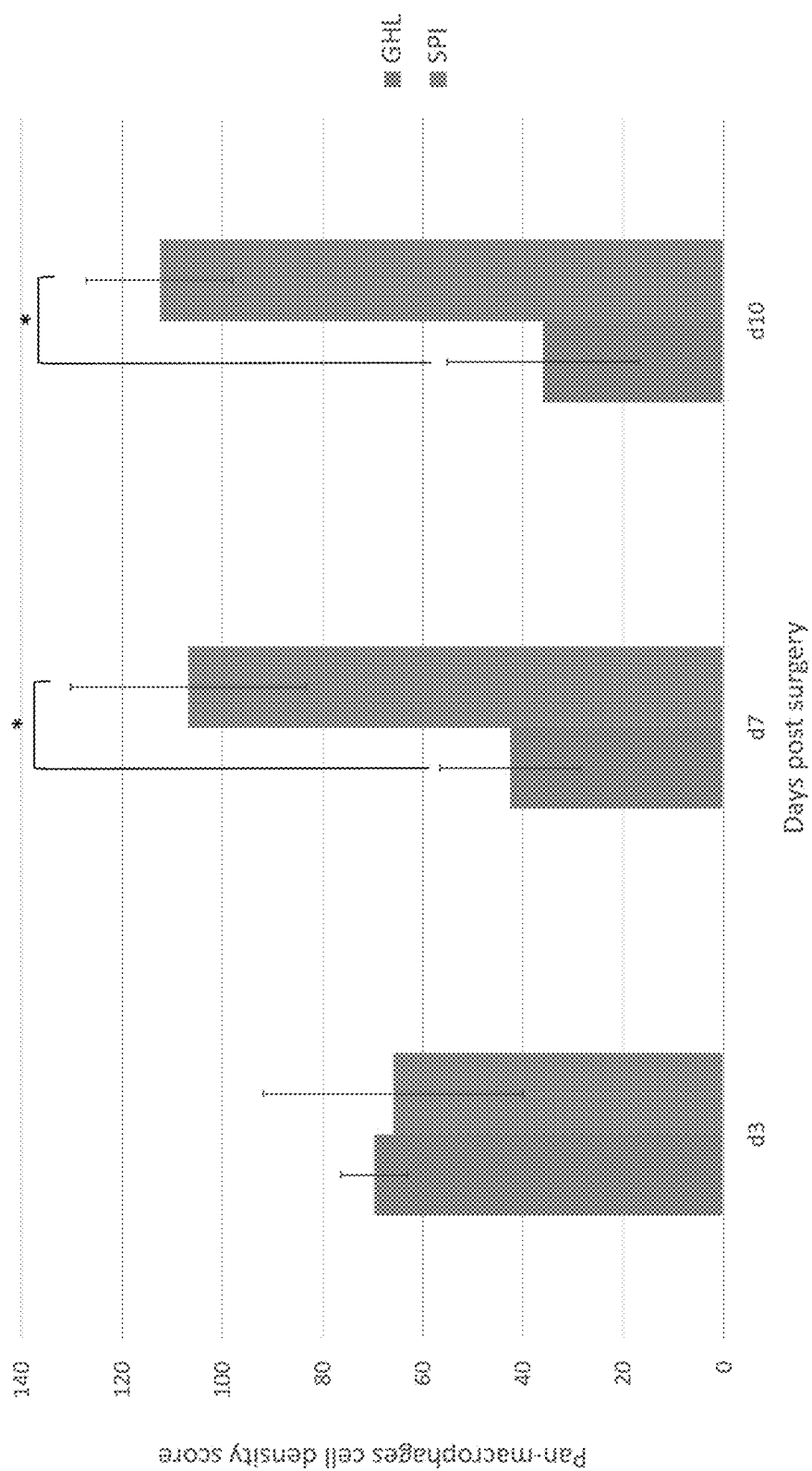
FIG. 13 is a graph showing the results of experiments investigating the inflammatory response of the body to a GHL scaffold and a regularly spun SPI scaffold, measured by pan-macrophage cell density score at 3, 7, and 10 days post-surgery. Single asterisk denotes the p value of equal or less than 0.05. A p-value of less than 0.05 indicates that two groups of comparison are significantly different with a certainty of 95%.
Figure 14:
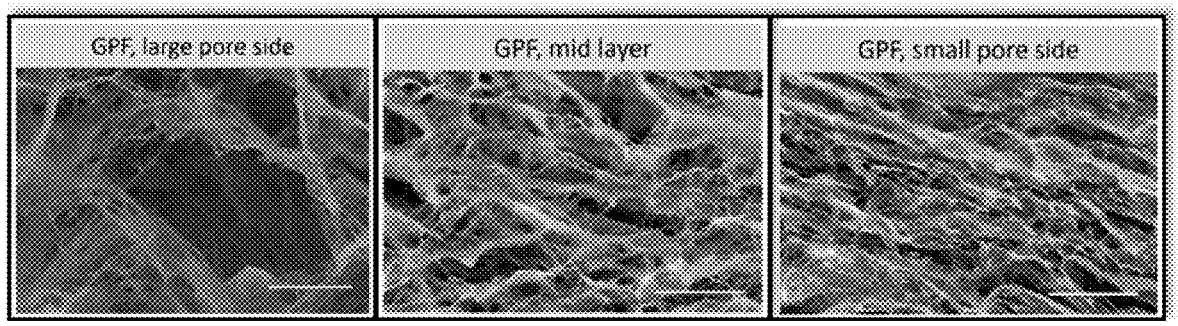
FIG. 14 depicts the results of experiments demonstrating that exemplary graded scaffolds of the present invention comprise three layers of distinct pore sizes.
Figure 14:
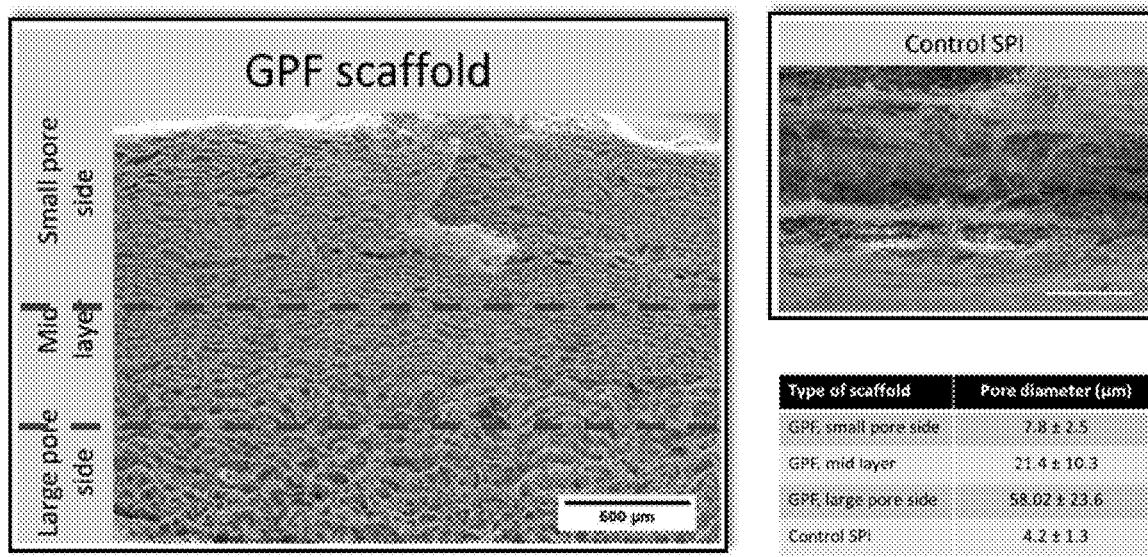
Figure 14:
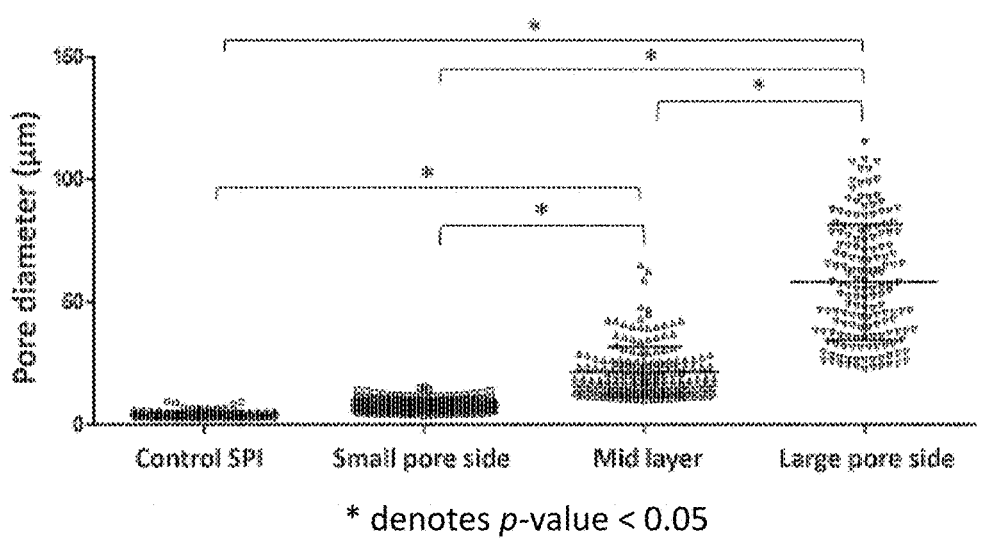
Figure 15:
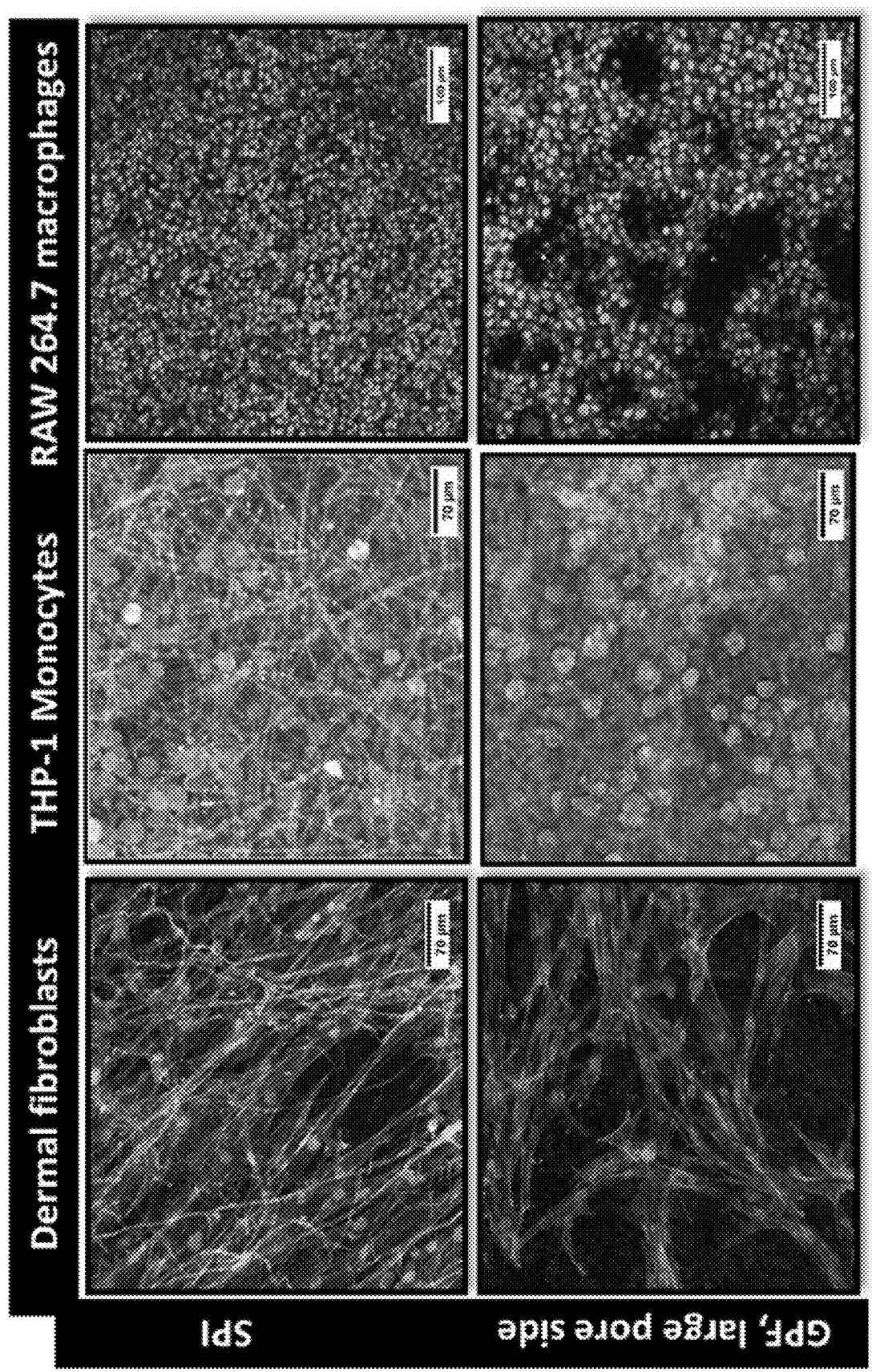
FIG. 15 depicts the results of experiments comparing the attachment and proliferation of human dermal fibroblasts, THP-1 monocytes, and RAW 264.7 macrophages in a regularly spun SPI scaffold and the large pore region of a graded porous fibrous (GPF) scaffold. Cell nuclei have been stained blue with DAPI; actin filaments have been stained greed with phalloidin.
Figure 16:
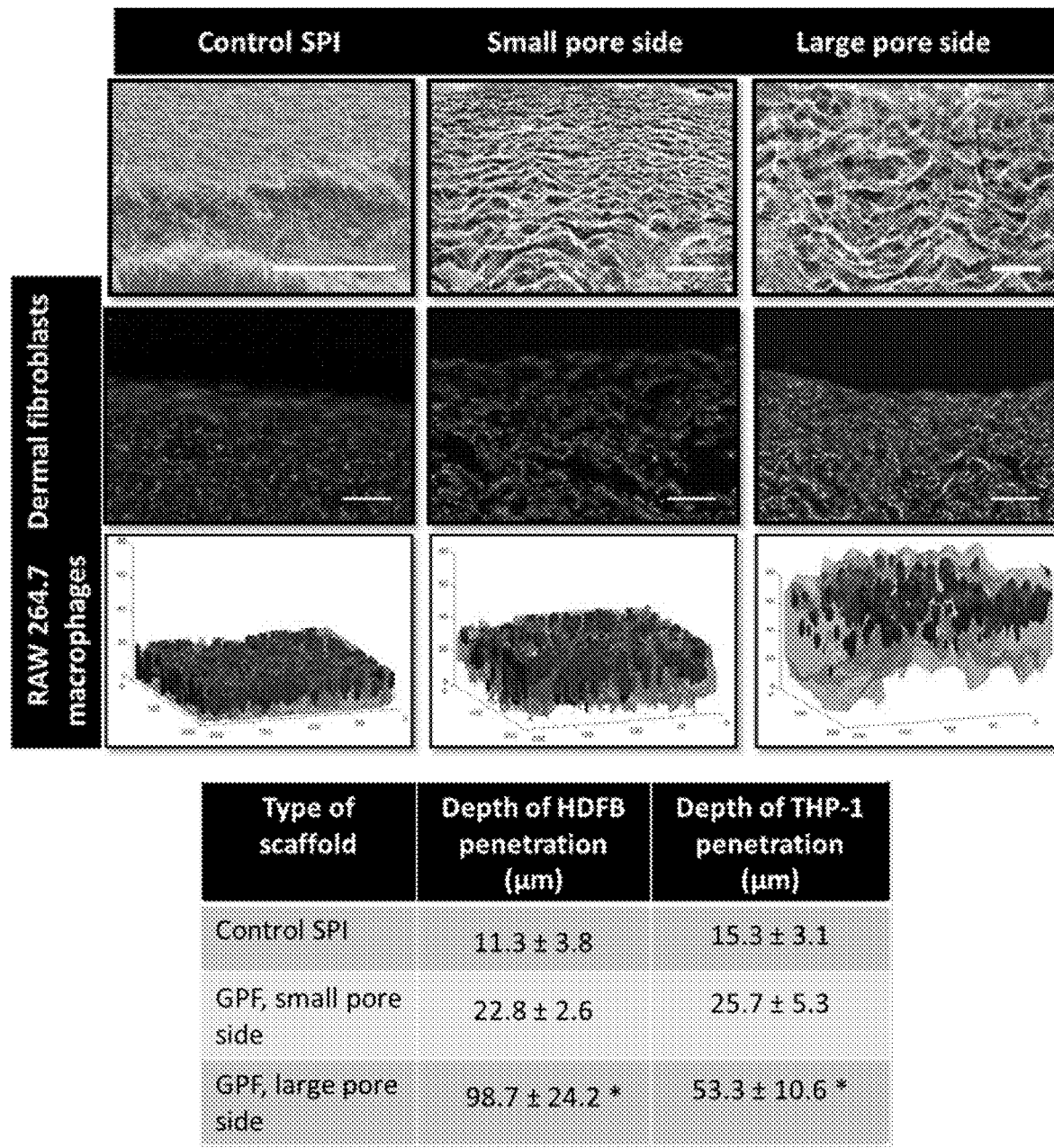
FIG. 16 depicts the results of experiments demonstrating that the large pore region of a GPF scaffold supports differential penetration of dermal fibroblasts. Dermal fibroblasts and RAW 264.7 macrophages cultured in regularly spun SPI scaffold and the small pore region of a GPF scaffold are provided for comparison. Cell nuclei have been stained blue with DAPI; actin filaments have been stained greed with phalloidin.
Figure 17:
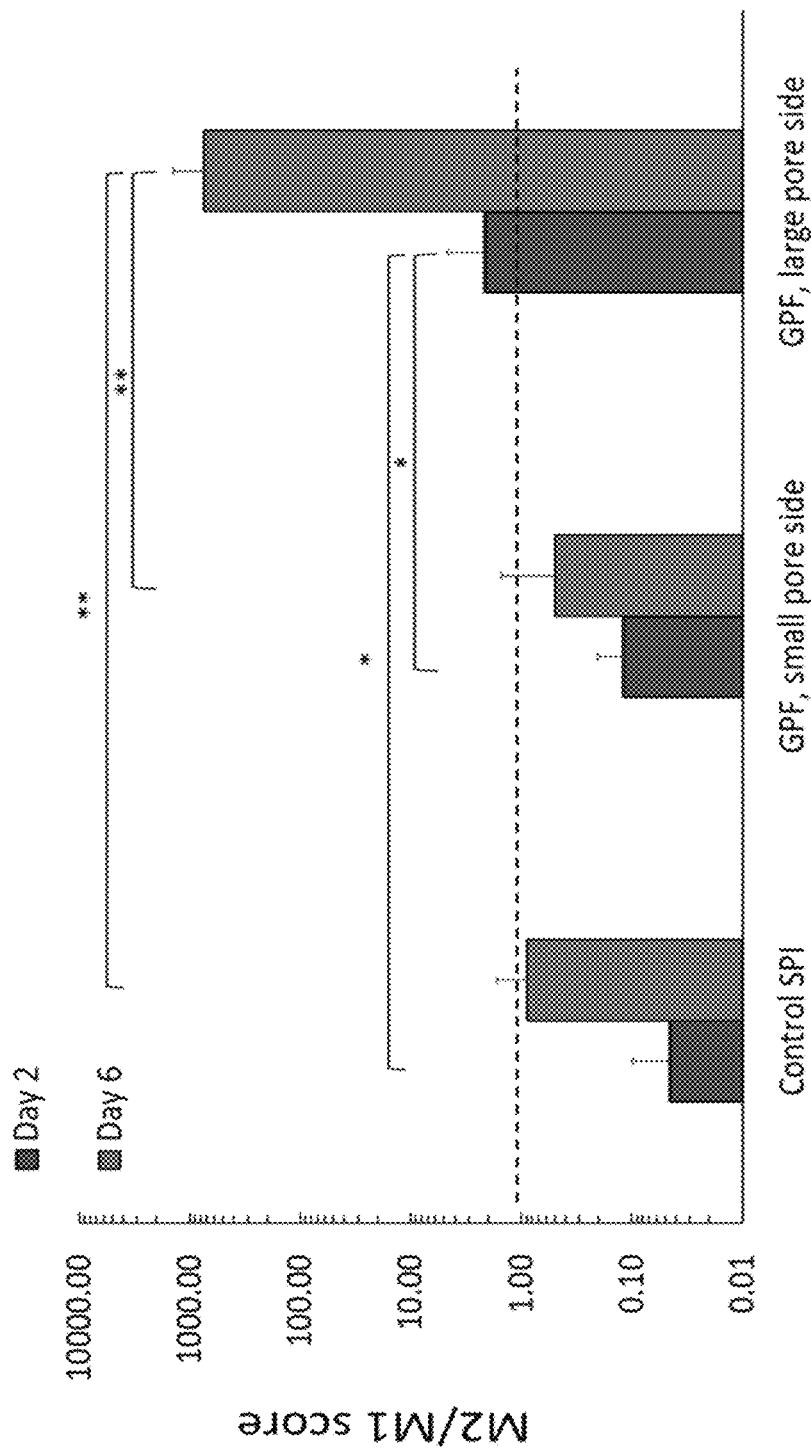
FIG. 17 depicts the results of experiments demonstrating that the large pore size of the GPF scaffolds enhances THP-1 macrophage polarization towards the pro-healing phenotype as early as Day 2 of culture. THP-1 macrophages cultured in a regularly spun SPI scaffold and the small pore region of a GP scaffold are provided for comparison. The M2/M1 score is defined as the sum of the expression levels of M1 genes (TNFα, IL6) divided by the sum of the expression levels of M2 genes (MRC1, CCL17).
Figure 18:
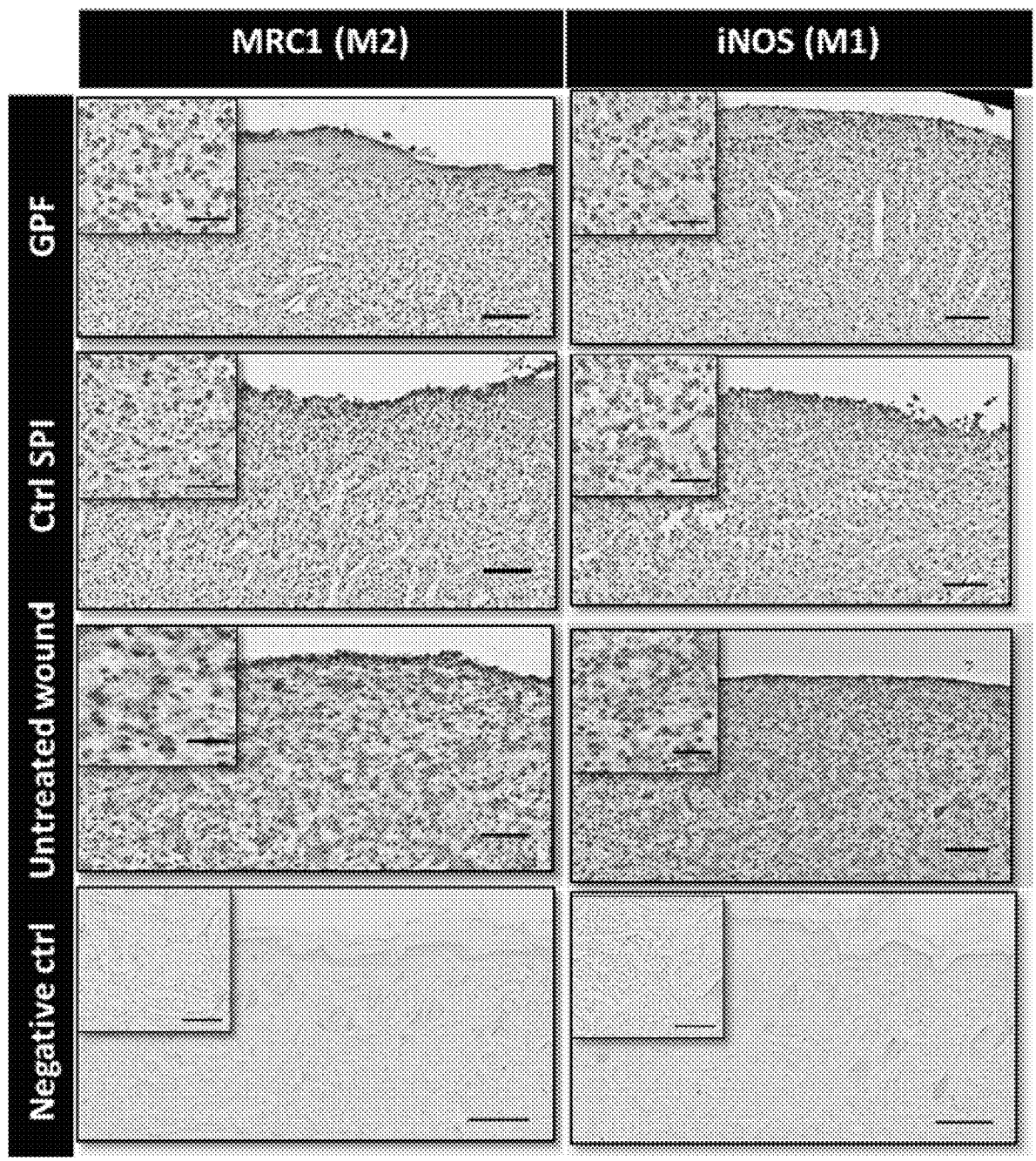
FIG. 18 depicts the results of treating wounds using exemplary GPF scaffolds compared to a wound treated with a regularly spun SPI scaffold and an untreated wound bed. Immunohistochemistry staining of pro-healing (M2) and pro-inflammatory (M1) antibodies in brown 7 days post-surgery. Scale bar is 250 μm, 100 μm in insets.
Figure 19:
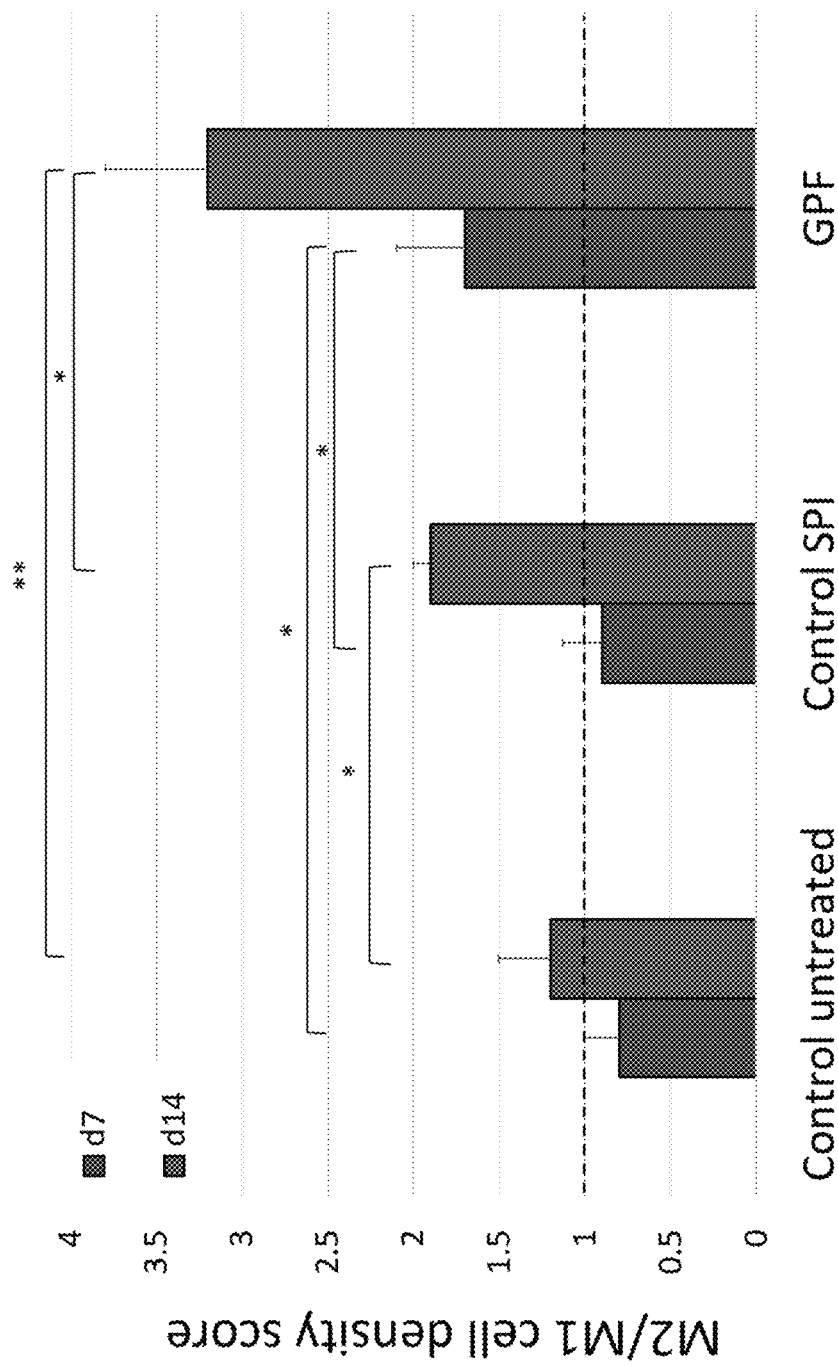
FIG. 19 depicts the results of experiments demonstrating that the GPF scaffolds implanted in a wound enhance polarization of macrophages towards the pro-healing phenotype. Macrophages in a regularly spun SPI scaffold implanted in a wound and an untreated wound are provided for comparison. The M2/M1 score is defined as the mean of the number of macrophages immunostained with anti-MRC1 divided by the mean of the number of macrophages immunostained with anti-iNOS, each normalized to the sampled area.

Staining of the tissues with a pan-macrophage antibody that identifies all macrophages present in the area adjacent to the collagenous capsule surrounding the scaffolds revealed a significantly lower number of macrophages targeting the GHL scaffold compared to the control SPI group 10 days post operation (FIG. 8A, FIG. 8B).

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A scaffold comprising:
a material having a gradient of pores comprising plant protein fibers having a first surface, a second surface, and a thickness therebetween;
wherein the average pore size at the first surface is smaller than the average pore size at the second surface;
wherein the average pore size gradually increases through the material thickness from the first surface to the second surface;
wherein the pores of the first surface prohibit the passage of cells; and
wherein the second surface is configured to allow cell penetration into the thickness of the material up to the first surface.

2. The scaffold of claim 1, wherein the plant protein is selected from the group consisting of: soy protein isolate, wheat gluten, corn zein, and pea protein.

3. The scaffold of claim 1, wherein the fibers have a diameter between 0.5 µm and 5 µm.

4. The scaffold of claim 1, wherein the scaffold has a thickness between 500 µm and 2000 µm.

5. The scaffold of claim 1, wherein the average pore size of the first surface is between 1 µm and 20 µm in diameter.

6. The scaffold of claim 1, wherein the average pore size of the second surface is between 10 µm and 200 µm.

7. The scaffold of claim 1, wherein the gradual increase of the average pore size is linear.

8. The scaffold of claim 1, wherein the gradual increase of the average pore size is nonlinear.

9. The scaffold of claim 1, wherein the scaffold is capable of supporting cell growth.

10. The scaffold of claim 1, further comprising at least one cell.

11. The scaffold of claim 1, further comprising at least one material selected from the group consisting of: fibronectin, laminin, collagen, glycoprotein, thrombospondin, elastin, fibrillin, mucopolysaccharide, glycolipid, heparin sulfate, chondroitin sulfate, keratin sulfate, glycosaminoglycan, hyaluronic acid, proteoglycan, vitronectin, poly-D-lysine, and polysaccharide.

12. The scaffold of claim 1, further comprising at least one material selected from the group consisting of poly(epsilon-caprolactone) (PCL), poly(lactic acid) (PLA), poly(glycolic acid) (PGA), copolymers poly (lactide-co-glycolide) (PLGA), polyaniline, and poly(ethylene oxide) (PEO).

* * * * *